(12) United States Patent
Seme et al.

(10) Patent No.: US 9,827,022 B2
(45) Date of Patent: *Nov. 28, 2017

(54) GROWTH MODULATION SYSTEM

(71) Applicant: K2M, Inc., Leesburg, VA (US)

(72) Inventors: Steven J. Seme, Savage, MN (US); Thomas J. Gisel, Chaska, MN (US)

(73) Assignee: K2M, LLC, Leesburg, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/875,901

(22) Filed: Oct. 6, 2015

(65) Prior Publication Data

US 2016/0022323 A1    Jan. 28, 2016

Related U.S. Application Data

(63) Continuation of application No. 12/560,199, filed on Sep. 15, 2009, now Pat. No. 9,168,071.

(51) Int. Cl.
*A61B 17/70* (2006.01)

(52) U.S. Cl.
CPC ...... *A61B 17/7053* (2013.01); *A61B 17/7014* (2013.01); *A61B 17/7022* (2013.01); *A61B 17/7041* (2013.01); *A61B 17/7079* (2013.01)

(58) Field of Classification Search
CPC ............ A61B 17/70; A61B 17/7014–17/7031; A61B 17/7053
USPC ....... 606/57, 60, 74, 90, 102–103, 105, 246, 606/254–259, 263–279
See application file for complete search history.

(56) References Cited

U.S. PATENT DOCUMENTS

| | | |
|---|---|---|
| 2,774,350 A | 9/1952 | Cleveland |
| 3,242,922 A | 3/1966 | Thomas |
| 3,352,226 A | 11/1967 | Nelsen |

(Continued)

FOREIGN PATENT DOCUMENTS

| | | |
|---|---|---|
| DE | 2644735 A1 | 4/1977 |
| DE | 2845647 A1 | 5/1980 |

(Continued)

OTHER PUBLICATIONS

Canadian Office Action dated Jul. 28, 2016, issued in Canadian Application No. 2,770,717.

(Continued)

*Primary Examiner* — Eduardo C Robert
*Assistant Examiner* — Michelle C Eckman
(74) *Attorney, Agent, or Firm* — Carter, DeLuca, Farrell & Schmidt, LLP (57) ABSTRACT

A spinal management system includes a stabilizing member adapted to extend substantially longitudinally along a target region of a spine tending to exhibit a defective curvature and a set of stabilizing anchors adapted for fixation to vertebrae and to receive the stabilizing member to secure the stabilizing member against substantial transverse translation relative to the vertebrae. The system also includes a first correction anchor adapted for fixation to a vertebra, a second correction anchor adapted for fixation to a vertebra, and a connection between the stabilizing member and the first correction anchor and between the first and second correction anchors adapted such that when the connection is tensioned a compressive force is selectively exerted between the first and second correction anchors.

9 Claims, 5 Drawing Sheets

(56) References Cited

U.S. PATENT DOCUMENTS

| | | | | |
|---|---|---|---|---|
| 3,648,691 | A | 3/1972 | Lumb et al. | |
| 3,693,616 | A | 9/1972 | Roaf et al. | |
| 3,865,105 | A | 2/1975 | Lode | |
| 4,024,588 | A | 5/1977 | Janssen et al. | |
| 4,078,559 | A * | 3/1978 | Nissinen | A61B 17/7053 606/258 |
| 4,257,409 | A | 3/1981 | Bacal et al. | |
| 4,269,178 | A | 5/1981 | Keene | |
| 4,274,401 | A * | 6/1981 | Miskew | A61B 17/7004 606/256 |
| 4,355,645 | A | 10/1982 | Mitani et al. | |
| 4,361,141 | A | 11/1982 | Tanner | |
| 4,369,769 | A | 1/1983 | Edwards | |
| 4,404,967 | A | 9/1983 | Bacal et al. | |
| 4,411,259 | A * | 10/1983 | Drummond | A61B 17/7002 606/105 |
| 4,411,545 | A | 10/1983 | Roberge | |
| 4,448,191 | A | 5/1984 | Rodnyansky et al. | |
| 4,505,268 | A | 3/1985 | Sgandurra | |
| 4,554,914 | A | 11/1985 | Kapp et al. | |
| 4,573,454 | A * | 3/1986 | Hoffman | A61B 17/7053 606/250 |
| 4,604,995 | A | 8/1986 | Stephens et al. | |
| 4,611,581 | A | 9/1986 | Steffee | |
| 4,611,582 | A | 9/1986 | Duff | |
| 4,634,445 | A | 1/1987 | Helal | |
| 4,648,388 | A | 3/1987 | Steffee | |
| 4,653,481 | A | 3/1987 | Howland et al. | |
| 4,658,809 | A | 4/1987 | Ulrich et al. | |
| 4,697,582 | A | 10/1987 | William | |
| 4,738,251 | A | 4/1988 | Plaza | |
| 4,773,402 | A * | 9/1988 | Asher | A61B 17/7002 606/250 |
| 4,805,602 | A | 2/1989 | Puno et al. | |
| 4,815,453 | A * | 3/1989 | Cotrel | A61B 17/7049 606/261 |
| 4,827,918 | A | 5/1989 | Olerud | |
| 4,854,311 | A | 8/1989 | Steffee | |
| 4,931,055 | A | 6/1990 | Bumpus et al. | |
| 4,936,848 | A | 6/1990 | Bagby | |
| 5,000,166 | A | 3/1991 | Karpf | |
| 5,005,562 | A | 4/1991 | Cotrel | |
| 5,011,484 | A | 4/1991 | Breard | |
| 5,030,220 | A | 7/1991 | Howland | |
| 5,042,982 | A | 8/1991 | Harms et al. | |
| 5,084,049 | A | 1/1992 | Asher et al. | |
| 5,092,866 | A | 3/1992 | Breard et al. | |
| 5,092,867 | A | 3/1992 | Harms et al. | |
| 5,127,912 | A | 7/1992 | Ray et al. | |
| 5,129,900 | A | 7/1992 | Asher et al. | |
| 5,133,716 | A | 7/1992 | Plaza | |
| 5,147,363 | A | 9/1992 | Harle | |
| 5,176,679 | A | 1/1993 | Lin | |
| 5,176,680 | A | 1/1993 | Vignaud et al. | |
| 5,181,917 | A | 1/1993 | Rogozinski | |
| 5,190,543 | A | 3/1993 | Schlapfer | |
| 5,196,014 | A | 3/1993 | Lin | |
| 5,207,678 | A | 5/1993 | Harms et al. | |
| 5,209,752 | A | 5/1993 | Ashman et al. | |
| 5,219,349 | A | 6/1993 | Krag et al. | |
| 5,242,443 | A | 9/1993 | Kambin | |
| 5,254,118 | A | 10/1993 | Mirkovic | |
| 5,257,994 | A | 11/1993 | Lin | |
| 5,259,398 | A | 11/1993 | Vrespa | |
| 5,282,862 | A | 2/1994 | Baker et al. | |
| 5,306,275 | A | 4/1994 | Bryan | |
| 5,312,404 | A | 5/1994 | Asher et al. | |
| 5,312,410 | A | 5/1994 | Miller et al. | |
| 5,312,420 | A | 5/1994 | Toso et al. | |
| 5,330,473 | A | 7/1994 | Howland | |
| 5,330,474 | A | 7/1994 | Lin | |
| 5,352,226 | A | 10/1994 | Lin | |
| 5,360,431 | A | 11/1994 | Puno et al. | |
| 5,366,455 | A | 11/1994 | Dove et al. | |
| 5,368,594 | A | 11/1994 | Martin et al. | |
| 5,380,323 | A | 1/1995 | Howland | |
| 5,380,325 | A | 1/1995 | Lahille et al. | |
| 5,382,248 | A | 1/1995 | Jacobson et al. | |
| 5,387,212 | A | 2/1995 | Yuan et al. | |
| 5,387,213 | A | 2/1995 | Breard et al. | |
| 5,391,168 | A | 2/1995 | Sanders et al. | |
| 5,397,363 | A | 3/1995 | Gelbard | |
| 5,413,576 | A * | 5/1995 | Rivard | A61B 17/7047 606/250 |
| 5,436,542 | A | 7/1995 | Petelin et al. | |
| 5,437,669 | A | 8/1995 | Yuan et al. | |
| 5,437,671 | A | 8/1995 | Lozier et al. | |
| 5,456,722 | A | 10/1995 | McLeod et al. | |
| 5,466,238 | A | 11/1995 | Lin | |
| 5,470,333 | A | 11/1995 | Ray | |
| 5,480,440 | A | 1/1996 | Kambin | |
| 5,486,174 | A | 1/1996 | Fournet-Fayard et al. | |
| 5,487,744 | A | 1/1996 | Howland | |
| 5,490,851 | A | 2/1996 | Nenov et al. | |
| 5,496,318 | A | 3/1996 | Howland et al. | |
| 5,498,262 | A | 3/1996 | Bryan | |
| 5,501,684 | A | 3/1996 | Schlapfer et al. | |
| 5,520,688 | A | 5/1996 | Lin | |
| 5,527,314 | A | 6/1996 | Brumfield et al. | |
| 5,534,002 | A | 7/1996 | Brumfield et al. | |
| 5,540,689 | A | 7/1996 | Sanders et al. | |
| 5,544,993 | A | 8/1996 | Harle | |
| 5,549,679 | A | 8/1996 | Kuslich | |
| 5,562,660 | A | 10/1996 | Grob | |
| 5,562,662 | A | 10/1996 | Brumfield et al. | |
| 5,569,246 | A | 10/1996 | Ojima et al. | |
| 5,575,791 | A | 11/1996 | Lin | |
| 5,584,626 | A | 12/1996 | Assmundson | |
| 5,586,983 | A | 12/1996 | Sanders et al. | |
| 5,591,165 | A | 1/1997 | Jackson | |
| 5,601,554 | A | 2/1997 | Howland et al. | |
| 5,609,592 | A | 3/1997 | Brumfield et al. | |
| 5,611,800 | A | 3/1997 | Davis et al. | |
| 5,620,443 | A | 4/1997 | Gertzbein et al. | |
| 5,630,816 | A | 5/1997 | Kambin | |
| 5,643,259 | A | 7/1997 | Sasso et al. | |
| 5,645,599 | A | 7/1997 | Samani | |
| 5,649,926 | A | 7/1997 | Howland | |
| 5,658,284 | A | 8/1997 | Sebastian et al. | |
| 5,672,175 | A | 9/1997 | Martin | |
| 5,676,703 | A | 10/1997 | Gelbard | |
| 5,702,395 | A | 12/1997 | Hopf | |
| 5,702,399 | A | 12/1997 | Kilpela et al. | |
| 5,702,452 | A | 12/1997 | Argenson et al. | |
| 5,704,936 | A | 1/1998 | Mazel | |
| 5,704,937 | A * | 1/1998 | Martin | A61B 17/025 606/102 |
| 5,713,898 | A | 2/1998 | Stucker et al. | |
| 5,716,355 | A | 2/1998 | Jackson et al. | |
| 5,725,582 | A | 3/1998 | Bevan et al. | |
| 5,728,097 | A | 3/1998 | Mathews | |
| 5,733,284 | A | 3/1998 | Martin | |
| 5,735,852 | A | 4/1998 | Amrein et al. | |
| 5,782,831 | A * | 7/1998 | Sherman | A61B 17/7079 606/103 |
| 5,797,910 | A * | 8/1998 | Martin | A61B 17/025 606/54 |
| 5,810,817 | A | 9/1998 | Roussouly et al. | |
| 5,810,819 | A | 9/1998 | Errico et al. | |
| 5,814,046 | A | 9/1998 | Hopf | |
| 5,885,285 | A | 3/1999 | Simonson | |
| 5,891,145 | A | 4/1999 | Morrison et al. | |
| 5,902,305 | A | 5/1999 | Beger et al. | |
| 5,910,142 | A | 6/1999 | Tatar | |
| 5,928,232 | A | 7/1999 | Howland et al. | |
| 5,938,663 | A | 8/1999 | Petreto | |
| 5,947,967 | A | 9/1999 | Barker | |
| 5,964,769 | A | 10/1999 | Wagner et al. | |
| 5,976,135 | A | 11/1999 | Sherman et al. | |
| 5,980,521 | A | 11/1999 | Montague et al. | |
| 5,984,924 | A | 11/1999 | Asher et al. | |
| 5,989,256 | A | 11/1999 | Kuslich et al. | |
| 6,015,409 | A | 1/2000 | Jackson | |

(56) References Cited

U.S. PATENT DOCUMENTS

| | | | |
|---|---|---|---|
| 6,033,412 A | 3/2000 | Losken et al. | |
| 6,039,738 A | 3/2000 | Sanders et al. | |
| 6,053,921 A | 4/2000 | Wagner et al. | |
| 6,066,140 A | 5/2000 | Gertzbein et al. | |
| 6,077,268 A | 6/2000 | Farris et al. | |
| 6,080,156 A | 6/2000 | Asher et al. | |
| 6,083,224 A | 7/2000 | Gertzbein et al. | |
| 6,086,590 A * | 7/2000 | Margulies | A61B 17/7053 606/263 |
| 6,101,678 A | 8/2000 | Malloy et al. | |
| 6,110,173 A | 8/2000 | Thomas, Jr. | |
| 6,123,706 A | 9/2000 | Lange | |
| 6,132,431 A | 10/2000 | Nilsson et al. | |
| 6,132,464 A | 10/2000 | Martin | |
| 6,136,000 A | 10/2000 | Louis et al. | |
| 6,176,861 B1 | 1/2001 | Bernstein et al. | |
| 6,231,575 B1 | 5/2001 | Krag | |
| 6,248,106 B1 | 6/2001 | Ferree | |
| 6,251,111 B1 | 6/2001 | Barker et al. | |
| 6,254,603 B1 | 7/2001 | Gertzbein et al. | |
| 6,261,288 B1 | 7/2001 | Jackson | |
| 6,273,914 B1 | 8/2001 | Papas | |
| 6,277,120 B1 * | 8/2001 | Lawson | A61B 17/7053 606/263 |
| 6,283,967 B1 | 9/2001 | Troxell et al. | |
| 6,293,949 B1 | 9/2001 | Justis et al. | |
| 6,296,643 B1 | 10/2001 | Hopf et al. | |
| 6,299,613 B1 | 10/2001 | Ogilvie et al. | |
| 6,325,805 B1 | 12/2001 | Ogilvie et al. | |
| 6,328,739 B1 | 12/2001 | Liu et al. | |
| 6,358,254 B1 | 3/2002 | Anderson | |
| 6,364,883 B1 | 4/2002 | Santilli | |
| 6,364,885 B1 | 4/2002 | Kilpela et al. | |
| 6,391,030 B1 | 5/2002 | Wagner et al. | |
| 6,402,749 B1 | 6/2002 | Ashman | |
| 6,402,752 B2 | 6/2002 | Schaffler-Wachter et al. | |
| 6,419,703 B1 | 7/2002 | Fallin et al. | |
| 6,423,065 B2 | 7/2002 | Ferree | |
| 6,451,019 B1 | 9/2002 | Zucherman et al. | |
| 6,458,131 B1 | 10/2002 | Ray | |
| 6,471,704 B2 | 10/2002 | Gertzbein et al. | |
| 6,488,683 B2 | 12/2002 | Lieberman | |
| 6,514,255 B1 * | 2/2003 | Ferree | A61B 17/7053 606/103 |
| 6,520,962 B1 | 2/2003 | Taylor et al. | |
| 6,537,276 B2 | 3/2003 | Metz-Stavenhagen | |
| 6,547,789 B1 | 4/2003 | Ventre et al. | |
| 6,551,320 B2 | 4/2003 | Lieberman | |
| 6,554,831 B1 | 4/2003 | Rivard et al. | |
| 6,562,038 B1 | 5/2003 | Morrison | |
| 6,565,569 B1 | 5/2003 | Assaker et al. | |
| 6,569,164 B1 | 5/2003 | Assaker et al. | |
| 6,579,292 B2 | 6/2003 | Taylor | |
| 6,579,319 B2 | 6/2003 | Goble et al. | |
| 6,582,433 B2 | 6/2003 | Yun | |
| 6,585,738 B1 | 7/2003 | Mangione et al. | |
| 6,589,243 B1 | 7/2003 | Viart et al. | |
| 6,602,254 B2 | 8/2003 | Gertzbein et al. | |
| 6,602,818 B2 | 8/2003 | Choi et al. | |
| 6,610,091 B1 | 8/2003 | Reiley | |
| 6,616,669 B2 | 9/2003 | Ogilvie et al. | |
| 6,623,484 B2 | 9/2003 | Betz et al. | |
| 6,626,906 B1 | 9/2003 | Young | |
| 6,626,909 B2 | 9/2003 | Chin | |
| 6,641,585 B2 | 11/2003 | Sato et al. | |
| 6,645,207 B2 | 11/2003 | Dixon et al. | |
| 6,651,320 B1 | 11/2003 | Yagi et al. | |
| 6,656,185 B2 | 12/2003 | Gleason et al. | |
| 6,669,729 B2 | 12/2003 | Chin | |
| 6,682,532 B2 | 1/2004 | Johnson et al. | |
| 6,682,533 B1 | 1/2004 | Dinsdale et al. | |
| 6,685,705 B1 | 2/2004 | Taylor | |
| 6,689,133 B2 | 2/2004 | Morrison et al. | |
| 6,709,435 B2 | 3/2004 | Lin | |
| 6,736,817 B2 | 5/2004 | Troxell et al. | |
| 6,749,612 B1 | 6/2004 | Conchy et al. | |
| 6,755,828 B2 * | 6/2004 | Shevtsov | A61B 17/8625 606/246 |
| 6,773,437 B2 | 8/2004 | Ogilvie et al. | |
| 6,802,844 B2 | 10/2004 | Ferree | |
| 6,811,567 B2 | 11/2004 | Reiley | |
| 6,835,207 B2 | 12/2004 | Zacouto et al. | |
| 6,840,127 B2 | 1/2005 | Moran | |
| 6,860,884 B2 | 3/2005 | Shirado et al. | |
| 6,887,241 B1 | 5/2005 | McBride et al. | |
| 6,902,580 B2 | 6/2005 | Fallin et al. | |
| 6,946,000 B2 | 9/2005 | Senegas et al. | |
| 6,966,910 B2 | 11/2005 | Ritland | |
| 6,966,930 B2 | 11/2005 | Arnin et al. | |
| 6,974,478 B2 | 12/2005 | Reiley et al. | |
| 6,986,771 B2 | 1/2006 | Paul et al. | |
| 7,008,423 B2 | 3/2006 | Assaker et al. | |
| 7,018,379 B2 | 3/2006 | Drewry et al. | |
| 7,029,475 B2 | 4/2006 | Panjabi | |
| 7,041,136 B2 | 5/2006 | Goble et al. | |
| 7,048,736 B2 | 5/2006 | Robinson et al. | |
| 7,051,451 B2 | 5/2006 | Augostino et al. | |
| 7,074,237 B2 | 7/2006 | Goble et al. | |
| 7,083,621 B2 | 8/2006 | Shaolian et al. | |
| 7,087,056 B2 | 8/2006 | Vaughan | |
| 7,090,698 B2 | 8/2006 | Goble et al. | |
| 7,104,992 B2 | 9/2006 | Bailey | |
| RE39,325 E | 10/2006 | Bryan | |
| 7,128,743 B2 | 10/2006 | Metz-Stavenhagen | |
| 7,137,986 B2 | 11/2006 | Troxell et al. | |
| 7,160,312 B2 | 1/2007 | Saadat | |
| 7,220,262 B1 | 5/2007 | Hynes | |
| 7,261,714 B2 | 8/2007 | Richelsoph | |
| 7,270,665 B2 | 9/2007 | Morrison et al. | |
| 7,290,347 B2 | 11/2007 | Augostino et al. | |
| 7,294,129 B2 | 11/2007 | Hawkins et al. | |
| 7,316,684 B1 | 1/2008 | Baccelli et al. | |
| 7,335,203 B2 | 2/2008 | Winslow et al. | |
| 7,338,490 B2 | 3/2008 | Ogilvie et al. | |
| 7,344,539 B2 | 3/2008 | Serhan et al. | |
| 7,361,196 B2 | 4/2008 | Fallin et al. | |
| 7,367,978 B2 | 5/2008 | Drewry et al. | |
| 7,406,775 B2 | 8/2008 | Funk et al. | |
| 7,445,635 B2 | 11/2008 | Fallin et al. | |
| 7,473,267 B2 | 1/2009 | Nguyen et al. | |
| 7,473,269 B1 | 1/2009 | Hynes | |
| 7,481,828 B2 | 1/2009 | Mazda et al. | |
| 7,507,242 B2 | 3/2009 | Triplett et al. | |
| 7,524,324 B2 | 4/2009 | Winslow et al. | |
| 7,566,345 B1 | 7/2009 | Fallin et al. | |
| 7,588,578 B2 | 9/2009 | Triplett et al. | |
| 7,588,590 B2 | 9/2009 | Chervitz et al. | |
| 7,591,836 B2 | 9/2009 | Dick et al. | |
| 7,594,924 B2 | 9/2009 | Albert et al. | |
| 7,611,526 B2 * | 11/2009 | Carl | A61B 17/70 606/248 |
| 7,618,453 B2 | 11/2009 | Goble et al. | |
| 7,618,455 B2 | 11/2009 | Goble et al. | |
| 7,621,955 B2 | 11/2009 | Goble et al. | |
| 7,648,521 B2 | 1/2010 | Hestad | |
| 7,658,753 B2 | 2/2010 | Carl et al. | |
| 7,674,293 B2 | 3/2010 | Kuiper et al. | |
| 7,678,136 B2 | 3/2010 | Doubler et al. | |
| 7,691,145 B2 | 4/2010 | Reiley et al. | |
| 7,708,762 B2 | 5/2010 | McCarthy et al. | |
| 7,717,940 B2 | 5/2010 | Woods et al. | |
| 7,717,942 B2 | 5/2010 | Schumacher | |
| 7,722,647 B1 | 5/2010 | Wang et al. | |
| 7,722,648 B2 | 5/2010 | Drewry et al. | |
| 7,753,937 B2 | 7/2010 | Chervitz et al. | |
| 7,758,581 B2 | 7/2010 | Chervitz et al. | |
| 7,771,474 B2 | 8/2010 | Cordaro | |
| 7,794,476 B2 | 9/2010 | Wisnewski | |
| 7,794,478 B2 | 9/2010 | Nilsson | |
| 7,799,054 B2 | 9/2010 | Kwak et al. | |
| 7,819,902 B2 | 10/2010 | Abdelgany et al. | |
| 7,833,252 B2 | 11/2010 | Justis et al. | |
| 7,837,714 B2 | 11/2010 | Drewry et al. | |
| 7,842,071 B2 | 11/2010 | Hawkes | |

(56) References Cited

U.S. PATENT DOCUMENTS

| | | | |
|---|---|---|---|
| 7,862,586 B2 | 1/2011 | Malek |
| 7,896,906 B2 | 3/2011 | Kwak et al. |
| 7,918,876 B2 | 4/2011 | Mueller et al. |
| 7,927,359 B2 | 4/2011 | Trautwein et al. |
| 7,931,676 B2 | 4/2011 | Veldman et al. |
| 7,935,134 B2 | 5/2011 | Reglos et al. |
| 7,942,902 B2 | 5/2011 | Schwab |
| 7,959,653 B2 | 6/2011 | Thramann et al. |
| 7,963,978 B2 | 6/2011 | Winslow et al. |
| 7,985,243 B2 | 7/2011 | Winslow et al. |
| 8,012,184 B2 | 9/2011 | Schlapfer et al. |
| 8,016,860 B2 | 9/2011 | Carl et al. |
| 8,021,400 B2 | 9/2011 | Marino et al. |
| 8,029,543 B2 | 10/2011 | Young et al. |
| 8,029,546 B2 | 10/2011 | Capote et al. |
| 8,034,078 B2 | 10/2011 | Laskowitz et al. |
| 8,034,084 B2 | 10/2011 | Landry et al. |
| 8,043,345 B2 | 10/2011 | Carl et al. |
| 8,048,113 B2 | 11/2011 | Winslow et al. |
| 8,052,722 B2 | 11/2011 | Winslow et al. |
| 8,066,743 B2 | 11/2011 | Young et al. |
| 8,070,775 B2 | 12/2011 | Winslow et al. |
| 8,070,776 B2 | 12/2011 | Winslow et al. |
| 8,075,594 B2 | 12/2011 | Purcell |
| 8,097,022 B2 | 1/2012 | Marik |
| 8,114,134 B2 | 2/2012 | Winslow et al. |
| 8,114,158 B2 | 2/2012 | Carl et al. |
| 8,118,837 B2 | 2/2012 | Lemoine |
| 8,147,524 B2 | 4/2012 | Piza Vallespir |
| 8,162,979 B2 | 4/2012 | Sachs et al. |
| 8,167,908 B2 | 5/2012 | Ely et al. |
| 8,192,471 B2 | 6/2012 | Ludwig et al. |
| 8,221,466 B2 | 7/2012 | Asaad et al. |
| 8,262,696 B2 | 9/2012 | Falahee |
| 8,292,934 B2 | 10/2012 | Justis et al. |
| 8,323,319 B2 | 12/2012 | Mazda et al. |
| 8,353,934 B2 | 1/2013 | Drewry et al. |
| 8,357,182 B2 | 1/2013 | Seme |
| 8,357,183 B2 | 1/2013 | Seme et al. |
| 8,361,117 B2 | 1/2013 | Michielli et al. |
| 8,394,124 B2 * | 3/2013 | Biyani ............... A61B 17/7022 |
| | | | 606/246 |
| 8,403,958 B2 | 3/2013 | Schwab |
| 8,414,614 B2 | 4/2013 | Firkins et al. |
| 8,414,617 B2 | 4/2013 | Young et al. |
| 8,470,001 B2 | 6/2013 | Trautwein et al. |
| RE44,392 E | 7/2013 | Hynes |
| 8,475,499 B2 | 7/2013 | Cournoyer et al. |
| 8,480,712 B1 | 7/2013 | Samuel et al. |
| 8,518,086 B2 | 8/2013 | Seme et al. |
| 8,920,472 B2 * | 12/2014 | Seme ..................... A61B 17/70 |
| | | | 606/250 |
| 9,113,959 B2 * | 8/2015 | Seme ..................... A61B 17/70 |
| 9,168,071 B2 | 10/2015 | Seme et al. |
| 9,333,009 B2 * | 5/2016 | Kroll ................. A61B 17/7014 |
| 2001/0037111 A1 | 11/2001 | Dixon et al. |
| 2002/0032442 A1 | 3/2002 | Altarac et al. |
| 2002/0133155 A1 | 9/2002 | Ferree |
| 2002/0143329 A1 | 10/2002 | Serhan et al. |
| 2002/0151978 A1 | 10/2002 | Zacouto et al. |
| 2003/0040746 A1 | 2/2003 | Mitchell et al. |
| 2003/0045878 A1 | 3/2003 | Petit et al. |
| 2003/0093117 A1 | 5/2003 | Saadat |
| 2003/0109881 A1 | 6/2003 | Shirado et al. |
| 2003/0114853 A1 | 6/2003 | Burgess et al. |
| 2003/0153915 A1 | 8/2003 | Nekozuka et al. |
| 2003/0220643 A1 | 11/2003 | Ferree |
| 2004/0006391 A1 | 1/2004 | Reiley |
| 2004/0049274 A1 | 3/2004 | Reiley |
| 2004/0049277 A1 | 3/2004 | Reiley |
| 2004/0097931 A1 | 5/2004 | Mitchell |
| 2004/0106921 A1 * | 6/2004 | Cheung ............... A61B 17/7001 |
| | | | 606/250 |
| 2004/0149065 A1 | 8/2004 | Moran |
| 2004/0167520 A1 | 8/2004 | Zucherman et al. |
| 2004/0215190 A1 | 10/2004 | Nguyen et al. |
| 2004/0230201 A1 | 11/2004 | Yuan et al. |
| 2004/0230304 A1 | 11/2004 | Yuan et al. |
| 2005/0027361 A1 | 2/2005 | Reiley |
| 2005/0033291 A1 | 2/2005 | Ebara |
| 2005/0033295 A1 | 2/2005 | Wisnewski |
| 2005/0043797 A1 | 2/2005 | Lee |
| 2005/0043799 A1 | 2/2005 | Reiley |
| 2005/0049705 A1 | 3/2005 | Hale et al. |
| 2005/0055096 A1 | 3/2005 | Serhan et al. |
| 2005/0080420 A1 | 4/2005 | Farris et al. |
| 2005/0080486 A1 | 4/2005 | Fallin et al. |
| 2005/0107789 A1 | 5/2005 | Sweeney |
| 2005/0113927 A1 | 5/2005 | Malek |
| 2005/0113928 A1 | 5/2005 | Cragg et al. |
| 2005/0131537 A1 | 6/2005 | Hoy et al. |
| 2005/0131538 A1 | 6/2005 | Chervitz et al. |
| 2005/0149030 A1 | 7/2005 | Serhan et al. |
| 2005/0154390 A1 | 7/2005 | Biedermann et al. |
| 2005/0165396 A1 | 7/2005 | Fortin et al. |
| 2005/0171538 A1 | 8/2005 | Sgier et al. |
| 2005/0177240 A1 | 8/2005 | Blain |
| 2005/0203509 A1 | 9/2005 | Chinnaian et al. |
| 2005/0203511 A1 | 9/2005 | Wilson-MacDonald et al. |
| 2005/0203514 A1 | 9/2005 | Jahng et al. |
| 2005/0203516 A1 | 9/2005 | Biedermann et al. |
| 2005/0209603 A1 | 9/2005 | Zucherman et al. |
| 2005/0216004 A1 | 9/2005 | Schwab |
| 2005/0228326 A1 | 10/2005 | Kalfas et al. |
| 2005/0228377 A1 | 10/2005 | Chao et al. |
| 2005/0234453 A1 | 10/2005 | Shaolian et al. |
| 2005/0240264 A1 | 10/2005 | Tokish et al. |
| 2005/0245929 A1 | 11/2005 | Winslow et al. |
| 2005/0261685 A1 | 11/2005 | Fortin et al. |
| 2005/0261770 A1 | 11/2005 | Kuiper et al. |
| 2005/0267470 A1 | 12/2005 | McBride |
| 2005/0267579 A1 | 12/2005 | Reiley et al. |
| 2006/0004449 A1 | 1/2006 | Goble et al. |
| 2006/0009767 A1 | 1/2006 | Kiester |
| 2006/0009847 A1 | 1/2006 | Reiley |
| 2006/0009849 A1 | 1/2006 | Reiley |
| 2006/0036246 A1 * | 2/2006 | Carl ..................... A61B 17/7053 |
| | | | 606/248 |
| 2006/0036256 A1 | 2/2006 | Carl et al. |
| 2006/0036259 A1 | 2/2006 | Carl et al. |
| 2006/0036323 A1 | 2/2006 | Carl et al. |
| 2006/0036324 A1 | 2/2006 | Sachs et al. |
| 2006/0047282 A1 | 3/2006 | Gordon |
| 2006/0058790 A1 | 3/2006 | Carl et al. |
| 2006/0058791 A1 | 3/2006 | Broman et al. |
| 2006/0058792 A1 | 3/2006 | Hynes |
| 2006/0064091 A1 | 3/2006 | Ludwig et al. |
| 2006/0084976 A1 | 4/2006 | Borgstrom et al. |
| 2006/0084996 A1 | 4/2006 | Metz-Stavenhagen |
| 2006/0085075 A1 | 4/2006 | McLeer |
| 2006/0116686 A1 | 6/2006 | Crozet |
| 2006/0142758 A1 | 6/2006 | Petit |
| 2006/0142760 A1 | 6/2006 | McDonnell |
| 2006/0149234 A1 | 7/2006 | de Coninck |
| 2006/0189984 A1 | 8/2006 | Fallin et al. |
| 2006/0200149 A1 | 9/2006 | Hoy et al. |
| 2006/0212034 A1 | 9/2006 | Triplett et al. |
| 2006/0217712 A1 | 9/2006 | Mueller et al. |
| 2006/0217715 A1 | 9/2006 | Serhan et al. |
| 2006/0217718 A1 | 9/2006 | Chervitz et al. |
| 2006/0229616 A1 | 10/2006 | Albert et al. |
| 2006/0241594 A1 | 10/2006 | McCarthy et al. |
| 2006/0241598 A1 | 10/2006 | Khalili |
| 2006/0247627 A1 | 11/2006 | Farris |
| 2006/0253118 A1 | 11/2006 | Bailey |
| 2006/0271050 A1 | 11/2006 | Piza Vallespir |
| 2006/0276787 A1 | 12/2006 | Zubok et al. |
| 2006/0293660 A1 * | 12/2006 | Lewis ................. A61B 17/7056 |
| | | | 606/276 |
| 2006/0293663 A1 | 12/2006 | Walkenhorst et al. |
| 2007/0005062 A1 | 1/2007 | Lange et al. |
| 2007/0005063 A1 * | 1/2007 | Bruneau ............. A61B 17/7031 |
| | | | 606/279 |
| 2007/0016296 A1 | 1/2007 | Triplett et al. |

(56) References Cited

U.S. PATENT DOCUMENTS

| | | |
|---|---|---|
| 2007/0055373 A1 | 3/2007 | Hudgins et al. |
| 2007/0073293 A1 | 3/2007 | Martz et al. |
| 2007/0079517 A1 | 4/2007 | Augostino et al. |
| 2007/0083200 A1 | 4/2007 | Gittings et al. |
| 2007/0093814 A1 | 4/2007 | Callahan et al. |
| 2007/0093833 A1 | 4/2007 | Kuiper et al. |
| 2007/0161987 A1 | 7/2007 | Capote et al. |
| 2007/0161994 A1 | 7/2007 | Lowery et al. |
| 2007/0162002 A1 | 7/2007 | Tornier |
| 2007/0167946 A1 | 7/2007 | Triplett et al. |
| 2007/0167947 A1 | 7/2007 | Gittings |
| 2007/0168035 A1 | 7/2007 | Koske |
| 2007/0185492 A1 | 8/2007 | Chervitz et al. |
| 2007/0191846 A1 | 8/2007 | Bruneau et al. |
| 2007/0198014 A1 | 8/2007 | Graf et al. |
| 2007/0213716 A1 | 9/2007 | Lenke et al. |
| 2007/0219556 A1 | 9/2007 | Altarac et al. |
| 2007/0225712 A1 | 9/2007 | Altarac et al. |
| 2007/0225713 A1 | 9/2007 | Altarac et al. |
| 2007/0233075 A1 | 10/2007 | Dawson |
| 2007/0233090 A1 | 10/2007 | Naifeh et al. |
| 2007/0233093 A1* | 10/2007 | Falahee ............... A61B 17/683 606/86 A |
| 2007/0238335 A1 | 10/2007 | Veldman et al. |
| 2007/0270803 A1 | 11/2007 | Giger et al. |
| 2007/0270805 A1 | 11/2007 | Miller et al. |
| 2007/0270817 A1 | 11/2007 | Rezach |
| 2007/0270836 A1 | 11/2007 | Bruneau et al. |
| 2007/0270837 A1 | 11/2007 | Eckhardt et al. |
| 2007/0270838 A1 | 11/2007 | Bruneau et al. |
| 2007/0270967 A1 | 11/2007 | Fallin et al. |
| 2007/0276374 A1 | 11/2007 | Broman et al. |
| 2007/0288011 A1 | 12/2007 | Logan |
| 2007/0288024 A1* | 12/2007 | Gollogly ............... A61B 17/68 606/281 |
| 2008/0015577 A1* | 1/2008 | Loeb ............... A61B 17/7059 606/330 |
| 2008/0021466 A1 | 1/2008 | Shadduck et al. |
| 2008/0021469 A1 | 1/2008 | Holt |
| 2008/0027436 A1 | 1/2008 | Cournoyer et al. |
| 2008/0045954 A1 | 2/2008 | Reiley et al. |
| 2008/0051784 A1* | 2/2008 | Gollogly ............ A61B 17/7014 606/279 |
| 2008/0065069 A1* | 3/2008 | Betz ............... A61B 17/7055 606/250 |
| 2008/0077143 A1 | 3/2008 | Shluzas |
| 2008/0086213 A1 | 4/2008 | Reiley |
| 2008/0091202 A1 | 4/2008 | Reiley |
| 2008/0091210 A1 | 4/2008 | Reiley |
| 2008/0091268 A1 | 4/2008 | Reiley |
| 2008/0097437 A1 | 4/2008 | Reiley |
| 2008/0097438 A1 | 4/2008 | Reiley |
| 2008/0097439 A1 | 4/2008 | Reiley |
| 2008/0097440 A1 | 4/2008 | Reiley et al. |
| 2008/0097441 A1 | 4/2008 | Hayes et al. |
| 2008/0097446 A1 | 4/2008 | Reiley et al. |
| 2008/0097609 A1 | 4/2008 | Reiley |
| 2008/0097612 A1 | 4/2008 | Reiley |
| 2008/0097613 A1 | 4/2008 | Reiley et al. |
| 2008/0132951 A1 | 6/2008 | Reiley et al. |
| 2008/0140202 A1* | 6/2008 | Allard ............... A61B 17/7011 623/17.13 |
| 2008/0167688 A1 | 7/2008 | Fauth et al. |
| 2008/0177326 A1 | 7/2008 | Thompson |
| 2008/0183209 A1* | 7/2008 | Robinson ........... A61B 17/7026 606/246 |
| 2008/0183212 A1 | 7/2008 | Veldman et al. |
| 2008/0195100 A1 | 8/2008 | Capote et al. |
| 2008/0195153 A1 | 8/2008 | Thompson |
| 2008/0195154 A1 | 8/2008 | Brown et al. |
| 2008/0200953 A1 | 8/2008 | Reiley et al. |
| 2008/0221622 A1 | 9/2008 | Triplett et al. |
| 2008/0228227 A1 | 9/2008 | Brown et al. |
| 2008/0234737 A1 | 9/2008 | Boschert |
| 2008/0234739 A1 | 9/2008 | Hudgins et al. |
| 2008/0262546 A1 | 10/2008 | Calvosa et al. |
| 2008/0269805 A1 | 10/2008 | Dekutoski et al. |
| 2008/0275507 A1 | 11/2008 | Triplett et al. |
| 2008/0292161 A1 | 11/2008 | Funk et al. |
| 2008/0300606 A1* | 12/2008 | Moorcroft ............. A61B 17/62 606/103 |
| 2008/0306535 A1 | 12/2008 | Winslow et al. |
| 2008/0306536 A1* | 12/2008 | Frigg ................ A61B 17/7002 606/246 |
| 2008/0319483 A1 | 12/2008 | Triplett et al. |
| 2008/0319484 A1 | 12/2008 | Fauth |
| 2008/0319485 A1 | 12/2008 | Fauth et al. |
| 2008/0319488 A1 | 12/2008 | Helgerson |
| 2008/0319489 A1 | 12/2008 | Triplett |
| 2009/0012565 A1* | 1/2009 | Sachs ................ A61B 17/7041 606/246 |
| 2009/0012566 A1 | 1/2009 | Fauth |
| 2009/0018583 A1 | 1/2009 | Song et al. |
| 2009/0024134 A1 | 1/2009 | Triplett et al. |
| 2009/0024135 A1 | 1/2009 | Triplett et al. |
| 2009/0024166 A1 | 1/2009 | Carl et al. |
| 2009/0024167 A1 | 1/2009 | Chervitz et al. |
| 2009/0024168 A1 | 1/2009 | Chervitz et al. |
| 2009/0024169 A1 | 1/2009 | Triplett et al. |
| 2009/0030459 A1 | 1/2009 | Hoy et al. |
| 2009/0030460 A1 | 1/2009 | Chervitz et al. |
| 2009/0030461 A1 | 1/2009 | Hoy et al. |
| 2009/0036929 A1 | 2/2009 | Reglos et al. |
| 2009/0048632 A1 | 2/2009 | Firkins et al. |
| 2009/0062864 A1 | 3/2009 | Ludwig et al. |
| 2009/0062915 A1 | 3/2009 | Kohm et al. |
| 2009/0069849 A1 | 3/2009 | Oh et al. |
| 2009/0082871 A1 | 3/2009 | Fallin et al. |
| 2009/0088802 A1 | 4/2009 | Fallin |
| 2009/0093820 A1 | 4/2009 | Trieu et al. |
| 2009/0099607 A1 | 4/2009 | Fallin et al. |
| 2009/0112207 A1 | 4/2009 | Walker et al. |
| 2009/0112262 A1 | 4/2009 | Pool et al. |
| 2009/0112263 A1 | 4/2009 | Pool et al. |
| 2009/0125062 A1 | 5/2009 | Arnin |
| 2009/0194206 A1 | 8/2009 | Jeon et al. |
| 2009/0204156 A1 | 8/2009 | McClintock et al. |
| 2009/0259256 A1 | 10/2009 | Miller |
| 2009/0281575 A1* | 11/2009 | Carls ................ A61B 17/7053 606/278 |
| 2010/0057129 A1 | 3/2010 | Goble et al. |
| 2010/0076493 A1 | 3/2010 | Fauth et al. |
| 2010/0082107 A1 | 4/2010 | Fauth et al. |
| 2010/0087880 A1 | 4/2010 | Fauth et al. |
| 2010/0100130 A1 | 4/2010 | Carl et al. |
| 2010/0100133 A1 | 4/2010 | Carl et al. |
| 2010/0106192 A1 | 4/2010 | Barry |
| 2010/0137913 A1 | 6/2010 | Khatchadourian et al. |
| 2010/0145392 A1* | 6/2010 | Dutoit .................. A61B 17/68 606/279 |
| 2010/0211071 A1* | 8/2010 | Lettmann ........... A61B 17/0401 606/60 |
| 2010/0249836 A1* | 9/2010 | Seme ................ A61B 17/7001 606/246 |
| 2010/0249837 A1 | 9/2010 | Seme et al. |
| 2010/0256684 A1 | 10/2010 | Seme et al. |
| 2010/0274286 A1 | 10/2010 | Blain et al. |
| 2010/0286730 A1 | 11/2010 | Gordon |
| 2010/0318129 A1* | 12/2010 | Seme ................ A61B 17/7001 606/254 |
| 2011/0054536 A1* | 3/2011 | Elsebaie ........... A61B 17/7001 606/264 |
| 2011/0060367 A1 | 3/2011 | Stauber |
| 2011/0066188 A1* | 3/2011 | Seme ................ A61B 17/7041 606/264 |
| 2011/0245830 A1* | 10/2011 | Zgonis ................ A61B 17/62 606/57 |
| 2011/0245836 A1* | 10/2011 | Hamada .............. A61B 17/02 606/90 |
| 2011/0245876 A1 | 10/2011 | Brumfield |
| 2011/0270314 A1* | 11/2011 | Mueller ............. A61B 17/704 606/264 |

(56) References Cited

U.S. PATENT DOCUMENTS

| | | | |
|---|---|---|---|
| 2011/0288551 A1* | 11/2011 | Walther | A61C 5/007 606/74 |
| 2011/0301645 A1* | 12/2011 | Connor | A61B 17/7016 606/263 |
| 2012/0109197 A1 | 5/2012 | Carl et al. | |
| 2012/0221057 A1 | 8/2012 | Zhang et al. | |
| 2012/0290014 A1* | 11/2012 | Parent | A61B 17/0642 606/279 |
| 2013/0123851 A1 | 5/2013 | Seme et al. | |
| 2013/0123853 A1* | 5/2013 | Seme | A61B 17/70 606/264 |
| 2013/0123854 A1* | 5/2013 | Kondrashov | A61B 17/7032 606/264 |
| 2013/0184757 A1 | 7/2013 | Seme et al. | |
| 2013/0211455 A1 | 8/2013 | Seme | |
| 2013/0231703 A1* | 9/2013 | Seme | A61B 17/70 606/252 |

FOREIGN PATENT DOCUMENTS

| | | |
|---|---|---|
| EP | 0260044 A1 | 3/1988 |
| EP | 0322334 A1 | 6/1989 |
| EP | 0418387 A1 | 3/1991 |
| EP | 1281361 A1 | 2/2003 |
| FR | 2697744 A1 | 5/1994 |
| FR | 2736535 A1 | 1/1997 |
| FR | 2781359 A1 | 1/2000 |
| FR | 2801492 A1 | 6/2001 |
| FR | 2872021 A1 | 12/2005 |
| FR | 2900563 A1 | 11/2007 |
| GB | 780652 A | 8/1957 |
| SU | 888968 A1 | 12/1981 |
| WO | 9213496 A1 | 8/1992 |
| WO | 2004017705 A2 | 3/2004 |
| WO | 2006010844 A1 | 2/2006 |
| WO | 2006017641 A2 | 2/2006 |
| WO | 2006136937 A2 | 12/2006 |
| WO | 2007051924 A1 | 5/2007 |
| WO | 2008086467 A2 | 7/2008 |
| WO | 2008154313 A1 | 12/2008 |
| WO | 2010053662 A1 | 5/2010 |
| WO | 2010056650 A1 | 5/2010 |
| WO | 2010111500 A2 | 9/2010 |

OTHER PUBLICATIONS

International Search Report and Written Opinion issued in PCT/US2010/047117, dated Dec. 2, 2010, 18 pages.

International Search Report and Written Opinion issued in PCT/US2005/027692, dated May 19, 2008, 4 pages.

International Search Report and Written Opinion issued in PCT/US2008/065979, dated Oct. 2, 2008, 7 pages.

International Search Report and Written Opinion issued in PCT/US2009/063833, dated Mar. 15, 2010, 14 pages.

International Application No. PCT/US2010/28684, filed Mar. 25, 2010, entitled Semi-Constrained Anchoring System.

U.S. Appl. No. 12/411,562, filed Mar. 26, 2009, entitled Semi-Constrained Anchoring System.

U.S. Appl. No. 12/485,796, filed Jun. 16, 2009 entitled Deformity Alignment System With Reactive Force Balancing.

Berry, James L. et al., A Morphometric Study of Human Lumbar and Selected Thoracic Vertebrae, 12 Spine 362 (1987).

Fujita, Masaru et al., A Biomechanical Analysis of Sublaminar and Subtransverse Process Fixation Using Metal Wires and Polyethylene Cables, 31 Spine 2202 (2006).

Girardi, Federico P. et al., Safety of Sublaminar Wires With Isola Instrumentation for the Treatment of Idiopathic Scoliosis, 25 Spine 691 (2000).

Molnar, Szabolcs et al., Ex Vivo and in Vitro Determination of the Axial Rotational Axis of the Human Thoracic Spine, 31 Spine E984 (2006).

Rajasekaran, S. et al., Eighteen-Level Analysis of Vertebral Rotation Following Harrington-Luque Instrumentation in Idiopathic Scoliosis, 76 J Bone Joint Surg Am. 104 (1994).

Wenger, Dennis R. et al., Biomechanics of Scoliosis Correction by Segmental Spinal Instrumentation, 7 Spine 260 (1982).

White III, Augustus A. et al., Biomechancis of the Spine 28-29, Tbl. 1-5 (2d ed. 1990).

Invitation to Pay Additional Fees and Partial Search Report issued in PCT/US2010/028684, dated Jun. 30, 2010.

International Search Report and Written Opinion issued in PCT/US2010/028684, dated Sep. 28, 2010, 19 pages.

International Search Report and Written Opinion issued in PCT/US2010/036375, dated Sep. 10, 2010, 16 pages.

European Search Report issued in EP Application No. 12154799, completed Mar. 2, 2012, 9 pages.

International Application No. PCT/US2008/065979, filed Jun. 5, 2008, entitled Medical Device and Method to Correct Deformity.

International Application No. PCT/US2009/063833, filed Nov. 10, 2009, entitled Growth Directed Vertebral Fixation System With Distractible Connector(s) and Apical Control.

International Search Report and Written Opinion issued in PCT/US2011/049693, dated Nov. 15, 2011, 16 pages.

Liljenqvist, Ulf R. et al., Analysis of Vertebral Morphology in Idiopathic Scoliosis with Use of Magnetic Resonance Imaging and Multiplanar Reconstruction, 84 J Bone Joint Surg Am. 359 (2002).

U.S. Appl. No. 12/411,558, filed Mar. 26, 2009, entitled Alignment System With Longitudinal Support Features.

U.S. Appl. No. 12/560,199, filed Sep. 15, 2009, entitled Growth Modulation System.

International Search Report and Written Opinion issued in PCT/US2012/065262, dated Feb. 5, 2013, 8 pages.

International Search Report and Written Opinion issued in PCT/US2012/040493, dated Aug. 21, 2012, 15 pages.

International Search Report and Written Opinion issued in PCT/US2013/065488, dated Feb. 18, 2014, 10 pages.

* cited by examiner

GROWTH MODULATION SYSTEM

CROSS REFERENCE TO RELATED APPLICATIONS

This application is a continuation of U.S. application Ser. No. 12/560,199, filed Sep. 15, 2009, the contents of which are hereby incorporated by reference in their entirety.

BACKGROUND

Various systems have been utilized to treat spinal deformities such as scoliosis, spondylolisthesis, and others. Primary surgical methods for treatment utilize instrumentation to correct a spinal deformity and implantable hardware systems to rigidly stabilize and maintain the correction. Many of these implantable hardware systems rigidly fix the spinal column to help facilitate fusion after the column has been moved to a corrected position. In some cases, the hardware systems are intended to allow growth or other movement of the corrected spinal column.

SUMMARY

Some aspects of embodiments described herein relate to a spinal management system including a stabilizing member adapted to extend substantially longitudinally along a target region of a spine tending to exhibit a defective curvature and a set of stabilizing anchors adapted for fixation to vertebrae and to receive the stabilizing member to secure the stabilizing member against substantial transverse translation relative to the vertebrae. The system also includes a first correction anchor adapted for fixation to a vertebra, a second correction anchor adapted for fixation to a vertebra, and a connection between the stabilizing member and the first correction anchor and between the first and second correction anchors adapted such that when the connection is tensioned a compressive force is selectively exerted between the first and second correction anchors.

This summary is not meant to be limiting in nature. While multiple embodiments are disclosed herein, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Various embodiments have been shown by way of example in the drawings and are described in detail below. As stated above, the intention, however, is not to limit the invention by providing such examples.

DETAILED DESCRIPTION

Some embodiments relate to a system for correcting spinal deformities, as well as associated methods and devices. In general terms, the system provides for selectively controlling growth of the spine by selectively applying compressive forces to the spine. In some applications, compressive forces are combined with lateral translational corrective force(s) and/or derotational corrective force(s) on a spinal column for halting or reversing defect progression. For example, growth modulation is used in some embodiments to help prevent further defect progression (e.g., further scoliotic degradation such as vertebral body wedging), as well as reverse the effects and/or root causes of abnormal growth under a defective model (e.g., uneven growth across the vertebra). In other words, whether skewed growth is viewed as a result of the spinal deformity and/or a contributing factor to spinal deformity, the system is adapted to modulate growth in order to better treat spinal deformity and encourage a more natural configuration of the spine. In some embodiments, vertebrae are selectively compressed along a first side 24B of the spinal column 24, for example along a convex aspect, or convex side of a defective curvature where the vertebrae have become inappropriately thickened. In some embodiments, such selective compression along the first side 24B helps slow growth along the first side 24B to facilitate better overall proportionality over time.

Various planes and associated directions are referenced in the following description, including a sagittal plane defined by two axes, one drawn between a head (superior) and tail (inferior) of the body and one drawn between a back (posterior) and front (anterior) of the body; a coronal plane defined by two axes, one drawn between a center (medial) to side (lateral) of the body and one drawn between a head (superior) and tail (inferior) of the body; and a transverse plane defined by two axes, one drawn between a back and front of the body and one drawn between a center and side of the body.

Also, the terms pitch, roll, and yaw are used, where roll generally refers to angulation, or rotation, in a first plane through which a longitudinal axis of a body orthogonally passes (e.g., rotation about a longitudinal axis corresponding to the spinal column), pitch refers to angulation, or rotation, in a second plane orthogonal to the first plane, and yaw refers to angulation, or rotation, in a third plane orthogonal to the first and second planes. In some embodiments, pitch is angulation in the sagittal plane, yaw is angulation in the coronal plane, and roll is angulation in the transverse plane. In various embodiments, changes in pitch, yaw, and/or roll occur concurrently or separately as desired. Moreover, as used herein, "lateral translation" is not limited to translation in the medial-lateral (or lateral-medial) direction unless specified as such.

Figure 1:
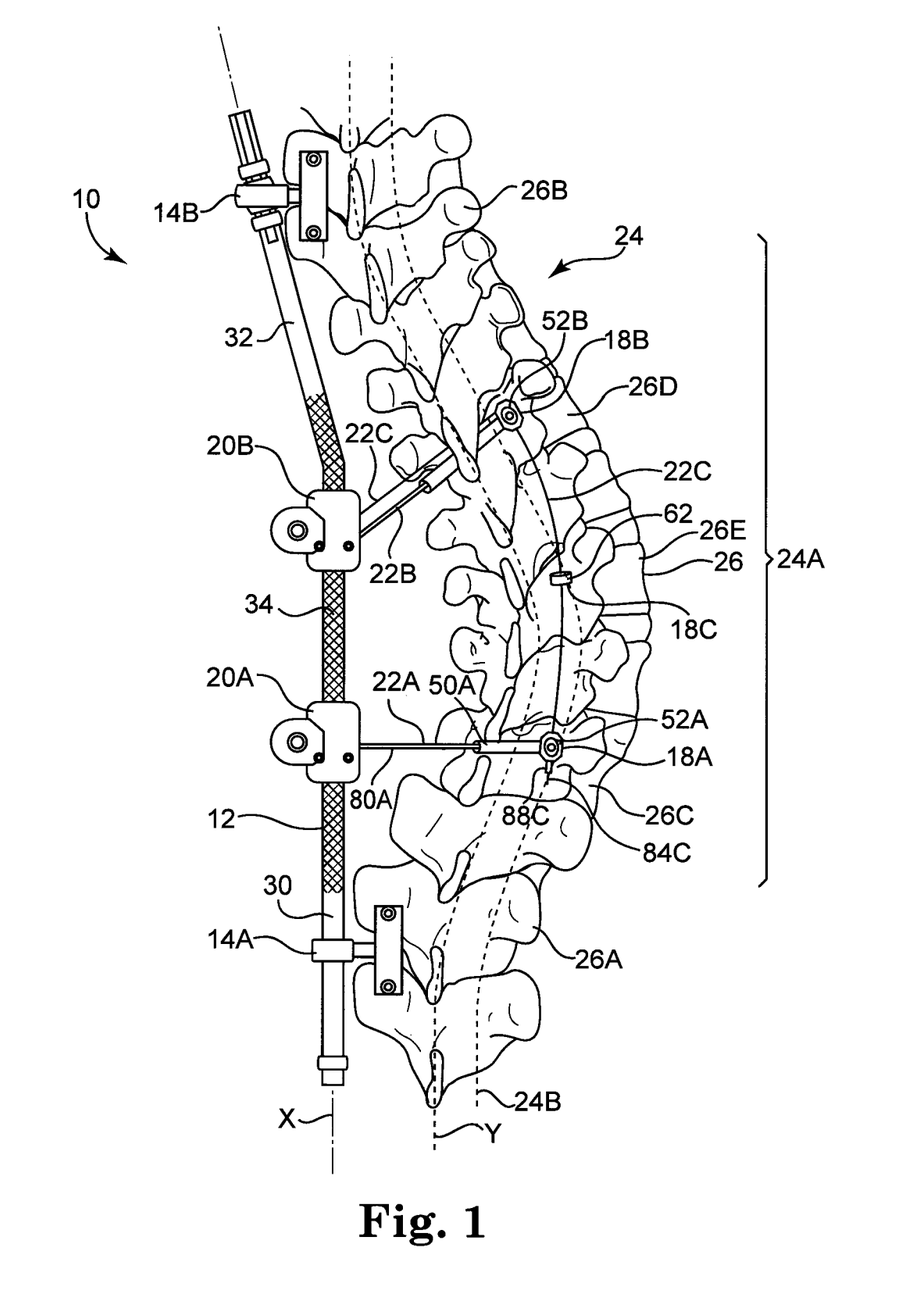
FIG. 1 shows an exemplary system for treating a spinal defect, according to some embodiments.

FIG. 1 is a perspective view of a system 10 for correcting a spinal deformity, according to some embodiments. The system 10 includes a stabilizing member 12; a plurality of stabilizing anchors 14, including a first stabilizing anchor 14A and a second stabilizing anchor 14B; a plurality of correction anchors 18 including a first correction anchor 18A and a second correction anchor 18B; a plurality of tensioners 20 including a first tensioner 20A and a second tensioner 20B; and a plurality of connectors 22 including a first connector 22A, a second connector 22B, and a third connector 22C. As shown, the system 10 is secured to a spinal column 24 formed of a plurality of vertebrae 26, including a first vertebra 26A, a second vertebra 26B, a third vertebra 26C, a fourth vertebra 26D, and a fifth vertebra 26E. The spinal column 24 also has a longitudinal axis Y that generally corresponds to the spinal cord and axis of transverse rotation of the spinal column 24.

Although the system 10 is shown in FIG. 1 with two stabilizing anchors 14, three correction anchors 18, two tensioners 20, and two connectors 22, more or fewer are implemented as appropriate in other embodiments. For example, in some embodiments a pair of stabilizing anchors 14 supports the stabilizing member 12 with a single correction anchor 18 and is secured to a vertebra 26 at an apex of a spinal deformation or other location, with a corresponding connector 22 and tensioner 20 coupled to the stabilizing member 12.

As shown in FIG. 1, however, the first and second correction anchors 18A, 18B are fixed to a target region 24A of the spinal column 24 tending to exhibit an abnormal, or defective curvature (e.g., scoliosis) in need of correction. The system 10 is optionally used to incrementally control growth of the spinal column 24 in the target region 24A and to adjust and/or maintain the spinal column 24 at a more natural curvature.

In some embodiments, a single adjustment is made to the system 10 to make a correction to a desired curvature, with the system 10 controlling spinal growth through incremental or gross adjustments as desired. In still other embodiments, the target region 24A of the spinal column 24 is adjusted to a more natural curvature using other, non-implanted hardware, prior to or in conjunction with implanting and securing the system 10 to the spinal column 24.

FIG. 1 shows the stabilizing member 12 having a bend according to some embodiments, although the stabilizing member 12 is substantially straight in other embodiments. In FIG. 1, the bend in the stabilizing member 12 is generally shown for illustrative purposes, where the stabilizing member 12 is optionally bent in one or more of the sagittal and coronal planes. The stabilizing member 12 is optionally formed of a variety of materials, including titanium alloy, cobalt chromium alloy, stainless steel or suitable polymeric materials. In other embodiments, the stabilizing member 12 is formed of superelastic material(s), such as a shape memory material.

In some embodiments, the stabilizing member 12 is substantially elongate and rigid, defining a substantially round cross-section with a mean diameter of about 6 mm and being formed of a suitable biocompatible material, such as titanium alloy ASTM F136. If desired, the stabilizing member 12 incorporates some flex, or springiness while substantially retaining its shape. The cross-sectional shape of the stabilizing member 12, including various portions thereof, is not limited to circular cross-sections and varies lengthwise in cross-section as desired. The stabilizing member 12 is adapted, or otherwise structured, to extend along the spinal column 24 at a desired spacing from the spinal column 24.

The stabilizing member 12 has a longitudinal axis X, as well as a first section 30, a second section 32, and an intermediate section 34 between the first and second sections 30, 32. Where the stabilizing member 12 is substantially straight, the longitudinal axis X is substantially straight. Where the stabilizing member 12 is substantially curved or angled, the longitudinal axis X is similarly curved or angled. The sections 30, 32, 34 of the stabilizing member 12 are optionally continuously formed or are formed as separate, connected parts as desired.

Additional examples of stabilizing members in accordance with some embodiments of the system 10 are set forth in U.S. application Ser. No. 11/196,952, filed on Aug. 3, 2005 and entitled DEVICE AND METHOD FOR CORRECTING A SPINAL DEFORMITY, as well as Ser. No. 12/134,058, filed on Jun. 5, 2008 and entitled MEDICAL DEVICE AND METHOD TO CORRECT DEFORMITY, the entire contents of both of which are hereby incorporated by reference.

FIG. 1 shows the pair of stabilizing anchors 14A, 14B which are adapted, or otherwise structured, to be mounted, or fixed to one or more vertebrae, such as the first and second vertebrae 26A, 26B. The first and second stabilizing anchors 14A, 14B are further adapted to receive, and include means for receiving, the stabilizing member 12 such that the stabilizing member 12 is secured laterally, against lateral translation relative to the first and second stabilizing anchors 14A, 14B.

Additional examples of stabilizing anchors in accordance with some embodiments of the system 10 are also described in U.S. patent application Ser. No. 12/411,562, entitled "Semi-Constrained Anchoring System", and filed Mar. 26, 2009, the entire contents of which are incorporated herein by reference.

The stabilizing anchors 14 are adapted to be secured to multiple locations, or points, or a single location, or point. In some embodiments, each of the stabilizing anchors 14 is secured to one or more support vertebrae, such as the first vertebra 26A and an additional vertebra 26 above or below the first vertebra (e.g., being secured to the pedicles of the L3-L4 vertebrae). In other embodiments, the first stabilizing anchor 14A is secured to a single support vertebra, such as the first vertebra 26A (e.g., laterally across the first vertebra 26A at the pedicles, or at a single point—such as a single pedicle—on the first vertebra 26A).

The stabilizing anchors 14 are adapted to receive the stabilizing member 12 and secure the stabilizing member 12 against substantial lateral or transverse translation relative to the support vertebrae to which they are attached, (e.g., the first and second vertebrae 26A, 26B). In this matter, the vertebrae 26A, 26B (as well as any secondary support vertebra to which the first stabilizing anchor 14A is secured) stabilize the system 10, providing a line of reference from which to adjust the curvature of the spinal column 24.

In some embodiments, the stabilizing member 12 is substantially prevented from translating in a direction that is substantially perpendicular to the longitudinal axis X of the stabilizing member 12 at each of the stabilizing anchors 14A, 14B. If desired, stabilizing member 12 is able to slide axially, or translate axially, along the longitudinal axis X, relative to the first and/or second stabilizing anchors 14A, 14B, and is free to change in at least one of pitch, yaw, and roll at each of the first and second stabilizing anchors 14A, 14B.

Figure 2:
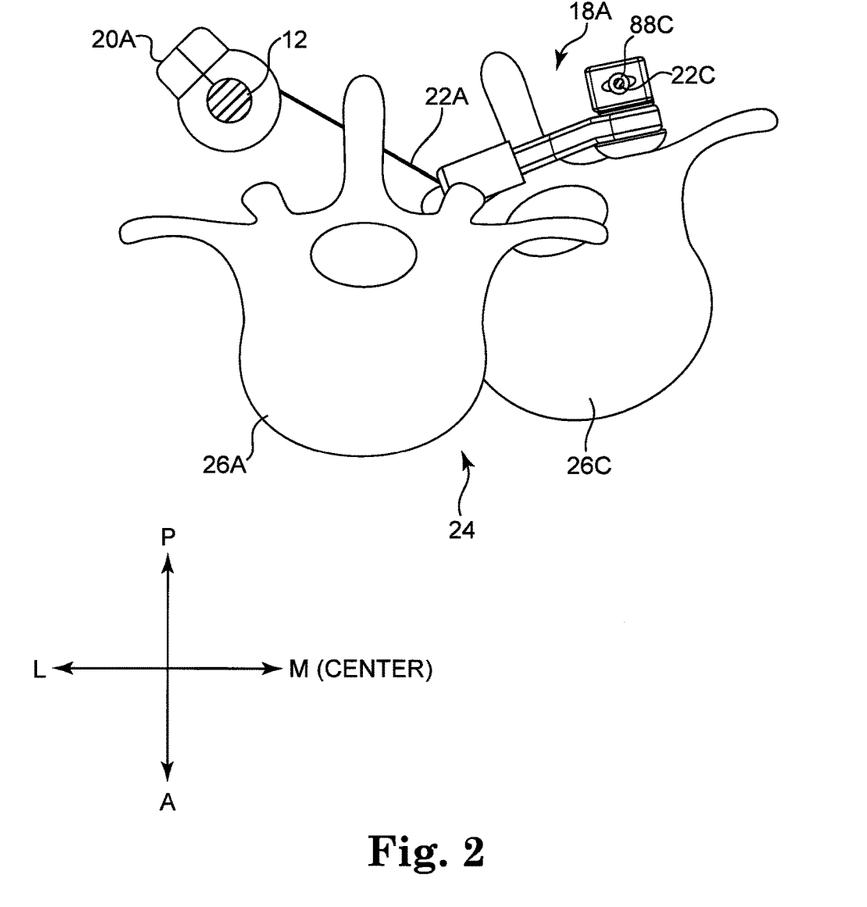
FIG. 2 is a transverse view of the system of FIG. 1 with some features not shown for ease of description.

FIG. 2 shows the system 10 from a transverse plane view, with portions of the spinal column 24 and system 10 not shown for illustrative purposes. For reference, the stabilizing member 12, the first correction anchor 18A, the first tensioner 20A, and the first connector 22A and the third connector 22C are shown along with the first vertebra 26A and third vertebra 26C.

As shown in FIG. 2, in some embodiments, the stabilizing member 12 is secured to the spinal column 24 at a preselected offset from a longitudinal axis of the spinal column 24. For example, the stabilizing member 12 is optionally secured at an offset along a medial-lateral axis ML, or right-left axis, and anterior-posterior axis AP, or back-front axis from the spinal column 24. In some embodiments, the stabilizing member 12 is secured on a left side of the spinal column 24, e.g., a side where the spinal column 24 tends to exhibit a defective, concave curvature, or aspect of a scoliotic spine. The offset is optionally selected such that corrective force(s) exerted by the system 10 result in a relative lateral translation (e.g., central or medial movement) and/or derotational shift (e.g., clockwise rotation from the bottom view of FIG. 2) of selected vertebrae 26 of the spinal column 24 (relative anterior-posterior movement of selected vertebrae 26 can also be accomplished) such that the spinal column 24 exhibits a more natural position. In some embodiments, the system 10 is adapted to exhibit reactive force balancing upon application of corrective forces, for example as set forth in U.S. application Ser. No. 12/485,796, filed on Jun. 16, 2009, and entitled DEFORMITY ALIGNMENT SYSTEM WITH REACTIVE FORCE BALANCING, the entire contents of which is incorporated herein by reference.

Figure 3:
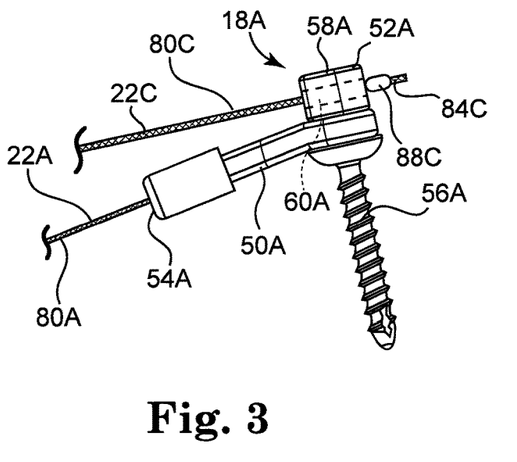
FIG. 3 is a front view of a correction anchor and connectors of the system of FIG. 1.

FIG. 3 shows the first correction anchor 18A, also described as an anchor arm, which is adapted to be fixed, and provides means for fixation, to a third vertebra 26C (FIG. 1). As previously described, the first correction anchor 18A is fixed to a target region 24A of the spinal column 24 (FIG. 1) having an abnormal curvature in need of correction.

The first and second correction anchors 18A, 18B are optionally substantially similar, and thus various features of both the first and second correction anchors 18A, 18B are described in association with the first correction anchor 18A. Features of the first correction anchor 18A are designated with reference numbers followed by an "A" and similar features of the second correction anchor 18B are designated with similar reference numbers followed by a "B."

The first correction anchor 18A includes an arm 50A and a head 52A and is generally L-shaped upon assembly of the arm 50A and head 52A. In some embodiments, the arm 50A extends from the head 52A to a terminal coupler 54A and is disposed generally perpendicular to the head 52A. In some embodiments, the arm 50A includes a bend and/or extends at an angle from the head 52A. The arm 50A is optionally secured about, and rotatable relative to the head 52A and is adapted to extend across a vertebra, for example, from one side of the spinal column 24 to an opposite side of the spinal column 24. In some embodiments, the first correction anchor 18A is secured to the third vertebra 26C (FIG. 1) such that the arm 50A extends across the third vertebra 26C either adjacent to the spinous processes or through a hole or hollowed portion in the spinous processes (not shown) of the third vertebra 26C. The first correction anchor 50A optionally includes means for securing the first correction anchor 50A to a second vertebral body location on the spinal column 24 (e.g., an aperture in the arm 50A for receiving a bone screw that is, in turn, secured to same vertebra or a different vertebra than the head 52A).

As shown in FIG. 3, the first connector 22A forms a connection between the stabilizing member 12 and the first correction anchor 18A, the first connector 22A being secured to the first correction anchor 18A, and in particular, through the terminal coupler 54A of the arm 50A, although a variety of manners and locations securing the first connector 22A to the first correction anchor 18A are contemplated.

In some embodiments, the head 52A of the correction anchor 18A is adapted, or is otherwise structured, to be fixed to a portion of the third vertebra 26C, such as a pedicle of the third vertebra 26C. The head 52A includes a body portion 56A and a cap portion 58A. The head 52A optionally includes and/or is adapted to work in conjunction with any of a variety of structures capable of engaging the third vertebra 26C. For example, the body portion 56A is optionally configured as a pedicle screw. In some embodiments the cap portion 58A includes one or more channels 60A for receiving one of the connectors 22, such as the third connector 22C. In some embodiments, the channel 60A is sized to slidably receive two or more of the connectors 22.

Assembly of the first correction anchor 18A includes receiving the arm 50A on the body portion 56A of the head 52A and screwing or otherwise securing the cap portion 58A onto the body portion 56A. In some embodiments, the first correction anchor 18A is substantially rigid.

Figure 4:
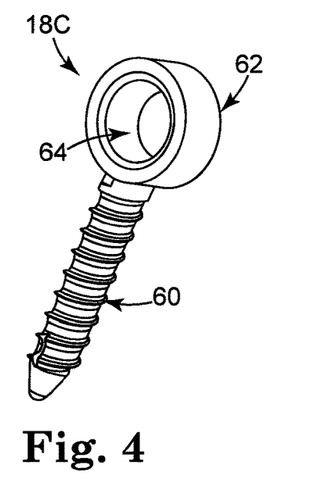
FIG. 4 is a perspective view of another correction anchor of the system of FIG. 1.

FIG. 4 shows the third correction anchor 18C, also described as a guide anchor, the third correction anchor 18C being of a different design than the first and second correction anchors 18A, 18B. The third correction anchor 18C is adapted to be mounted to one or more vertebrae, such as the fifth vertebra 26E (FIG. 1), and to receive one or more of the connectors 22 (FIG. 1) such as the third connector 22C. The third correction anchor 18C is optionally formed of biocompatible metallic materials, such as titanium, stainless steel, and/or biocompatible polymeric materials, such as PEEK and/or composite materials.

The third correction anchor 18C includes a mounting portion 60 and a receptacle portion 62. The mounting portion 60 is adapted to secure the third correction anchor 18C to one or more vertebrae, taking the form of a pedicle screw in some embodiments. The receptacle portion 62 is generally ring-shaped and forms a passage 64 through which one or more of the connectors 22 is able to pass.

The first tensioner 20A is shown in FIG. 1, where the first tensioner 20A is substantially similar to the second tensioner 20B in some embodiments. Generally, the first tensioner 20A provides means for securing the first connector 22A to the stabilizing member 12. In some embodiments, the first tensioner 20A, also described as an adjustment mechanism or coupler, is further adapted to adjust, and provides means for adjusting the effective length of the first connector 22A.

Figure 5:
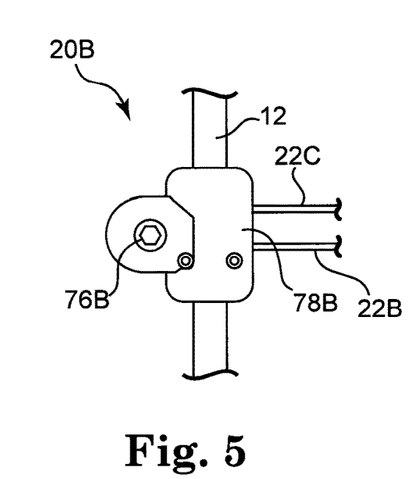
FIG. 5 is a side view of a tensioner and stabilizing member of the system of FIG. 1.
Figure 6:
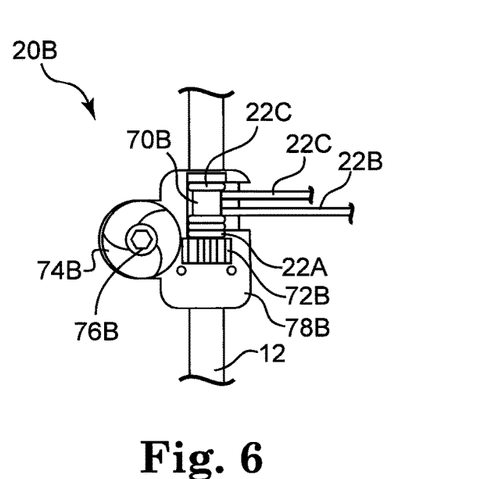
FIG. 6 is a side view of the tensioner of FIG. 5 with a housing portion removed.

FIGS. 5 and 6 show the second tensioner 20B, where FIG. 6 shows the second tensioner 20B with a portion removed to illustrate inner features thereof. In some embodiments, the second tensioner 20B provides means for securing the second and third connectors 22B, 22C to the stabilizing member 12. In some embodiments, the second tensioner 20B is further adapted to adjust, and provides means for adjusting length(s) of the second and/or third connectors 22B, 22C.

The first and second tensioners 20A, 20B are optionally substantially similar. Thus, various features of both the first and second tensioners 20A, 20B are described in association with the second tensioner 20B. Features of the first tensioner 20A are designated with reference numbers followed by an "A" and similar features of the second tensioner 20B are designated with the same reference numbers followed by a "B."

In some embodiments, the second tensioner 20B includes a reel 70B, a circumferential gear 72B surrounding the reel 70B, a vertical gear 74B in contact with the circumferential gear 72B, an actuation head 76B, and a housing 78B.

The reel 70B, as well as the circumferential gear 72B and vertical gear 74B are maintained at least partially within the housing 78B. In turn, the housing 78B is adapted to be secured to the stabilizing member 12. For example, the housing 78B optionally forms a central lumen through which the stabilizing member 12 is receivable. Upon inserting the stabilizing member 12 through the central lumen, the housing 78B is adapted to be clamped onto the stabilizing member 12.

In some embodiments, the housing 78B incorporates a clamshell design (e.g., a first portion adjustably secured to a second portion) adapted to be tightened onto the stabilizing member 12 (e.g., using one or more fasteners). Thus, in some embodiments, the second tensioner 20B is substantially fixed with respect to the stabilizing member 12. In other embodiments, however, the second tensioner 20B is movable with respect to the stabilizing member 12, for example being able to rotate about the stabilizing member 12.

The second and third connectors 22B, 22C are attached or secured to the reel 70B and pass out of the housing 78B through an appropriately sized opening in the housing 78B. Actuation of the vertical gear 74B via the actuation head 76B turns the circumferential gear 72B, which turns the reel 70B, thus winding (or unwinding, depending on the direction in which the reel 70B is turned) the second and third connectors 22B, 22C about the reel 70B. Rotation of the reel 70B in the appropriate direction draws the second connector 22B in toward the second tensioner 20B, pulling the second correction anchor 18B (FIG. 1) toward the second tensioner 20B according to some methods of correcting a spinal defect.

Upon turning of the reel 70B, the third connector 22C is also drawn in toward the second tensioner 20B, which compresses select portions of the spinal column 24 as described subsequently in greater detail. In other embodiments, the third connector 22C is secured to a different one of the plurality of tensioners 22 such that the effective lengths of the second and third connectors 22A, 22C are able to be independently adjusted. In still other embodiments, the second tensioner 20B is adapted to independently actuate the second and third connectors 22B, 22C, the tensioner 20B including multiple reel diameters and/or actuation components, for example, such that the second and third connectors 22B, 22C spool at different rates and/or spool independently. In still other embodiments, one or more portions of the second and third connectors 22B, 22C are secured together, for example being crimped or welded to a common connector (not shown), such that the second tensioner 20B simultaneously actuates the second and third connectors 22B, 22C by spooling the common connector.

From the foregoing, it should also be understood that the first connector 22A and the first tensioner 20A are similarly coupled, where actuation of the first tensioner 20A modifies an effective length of the first connector 22A, either drawing the first connector 22A toward the first tensioner 20A or letting out the first connector 22A away from the first tensioner 20A.

The connectors 22A, 22B, 22C are optionally substantially similar, and thus various features of the first, second, and third connectors 22A, 22B, 22C are described in association with the first connector 22A. Features of the first connector 22A are designated with reference numbers followed by an "A" and similar features of the second and third connectors 22B, 22C are designated with similar reference numbers followed by a "B" or a "C," respectively.

In some embodiments, the first connector 22A is substantially flexible such that the first connector 22A is able to be pivoted in multiple directions and/or be spooled or wound, for example. Suitable flexible materials for forming the first connector 22A include wire and stranded cables, monofilament polymer materials, multifilament polymer materials, multifilament carbon or ceramic fibers, and others. In some embodiments, the first connector 22A is formed of stainless steel, titanium alloy, or cobalt chromium wire or cable, although a variety of materials are contemplated.

As shown in FIG. 1, the first connector 22A, also described as a force directing member or a cable, is adapted to be secured to the first correction anchor 18A and the first tensioner 20A, the first connector 22A defining an effective length between the first tensioner 20A and the first correction anchor 18A, and thus the stabilizing member 12 (although, in some embodiments, the first connector 22A is secured directly to the stabilizing member 12). The first connector 22A has a body 80A and extends from a first end to a second end. In some embodiments, the body 80A is a single, substantially monolithic component (e.g., a single, continuous piece of cable). In other embodiments, the body 80A is formed of multiple components (e.g., both flexible and rigid components) secured together to form connections with various components of the system 10. As described, in some embodiments, the first tensioner 20A is adapted to modify, and provides means for modifying, the effective length of the first connector 22A.

As shown in FIG. 3, the third connector 22C also has a body 80C extending from a first end to a second end 84C. At the second end 84C, the third connector further includes an end piece 88C, such as a grommet, for securing the third connector 22C to the first correction anchor 18A.

In view of the foregoing, a manner of assembling the system 10 is described with reference to FIG. 1. The first and second tensioners 20A, 20B are secured to the stabilizing member 12. The first and second stabilizing anchors 14A, 14B are secured to the first and second vertebrae 26A, 26B, respectively. In some embodiments, the first and second vertebrae 26A, 26B are generally located posteriorly and anteriorly, proximate the upper and lower ends, of the target region 24A tending to exhibit defective curvature. In some embodiments, one or both of the first and second vertebrae 26A, 26B exhibit defective positioning (e.g., forming a part of the defective curvature of the target region 24A). In some embodiments, one or both of the first and second vertebrae 26A, 26B have a substantially natural orientation (e.g., being located substantially outside the area(s) of the spinal column 24 exhibiting defective curvature).

The stabilizing member 12 is received in the first and second stabilizing anchors 14A, 14B to secure the stabilizing member 12 against lateral translation relative to the spinal column 24. The first and second correction anchors 18A, 18B are secured to the third and fourth vertebrae 26C, 26D and the third correction anchor 18C is secured to the fifth vertebra 26E. As previously described, features of the first and second stabilizing anchors 14A, 14B are selected to limit pitch, yaw, roll, and axial sliding of the stabilizing member 12 as desired.

Assembly of the system 10 includes securing the first and second connectors 22A, 22B to the first and second correction anchors 18A, 18B, respectively. The first and second connectors 22A, 22B are also secured to the first and second tensioners 20A, 20B, respectively, such that the connectors 22A, 22B form connections between the stabilizing member 12 and the correction anchors 18A, 18B.

The first connector 22A is assembled to the first correction anchor 18A by securing the second end of the first connector 22A to the first correction anchor 18A proximate the terminal coupler 54A thereof. In some embodiments, the first connector 22A is secured at the terminal coupler 54A of the first correction anchor 18A, and extends along at least a portion of the arm 50A to the head 52A, although the first connector 22A is attached at any location along the arm 50A and/or the head 52A of the first correction anchor 18A as appropriate. The first connector 22A is securable to the first correction anchor 18A via a variety of methods, including welding, adhesives, tying, screw fixation, and/or other coupling means, for example.

The second connector 22B and the second correction anchor 18B are optionally secured or connected together using similar approaches.

The third connector 22C is passed through the head 52A of the first correction anchor 18A, through the receptacle portion 62 of the third correction anchor 18C, through the head 52B of the second correction anchor 18B, and to the second tensioner 20B to form a connection between the stabilizing member 12 and the third correction anchor 18C, as well as between the second and third correction anchors 18B, 18C. In some embodiments, the second end 84C of the third connector 22C is fitted with the end piece 88C, for example by clamping the end piece 88C onto the second end 84C, such that the second end 84C is unable to slide back through the head 52A of the first correction anchor 18A such that a tension on the third connector 22C directs the first correction anchor 18A toward the second correction anchor 18B.

In some embodiments, the first connector 22A extends to and is maintained by the first tensioner 20A, the first connector 22A being wound about its reel (not shown), thereby coupling the first tensioner 20A to the first correction anchor 18A as well as the stabilizing member 12. In some embodiments, the first connector 22A is secured to the reel via welding, screw fixation, adhesives, swaging, and/or other coupling means and/or is sufficiently wound about the reel for frictional retention of the first connector 22A on the reel.

The second and third connectors 22B, 22C and the second tensioner 20B are optionally secured or connected together using similar approaches. As previously mentioned, the third connector 22C is optionally secured to a third tensioner (not shown) or the second tensioner 20B includes means for independent adjustment of the connectors 22B, 22C as desired. For example, as shown in FIG. 1, the third connector 22C is connected from the stabilizing member 12 to the first correction anchor 18A through the second and third correction anchors 18B, 18C.

Upon assembly of the system 10, the first and second tensioners 20A, 20B are adjusted as desired to tension the respective connections and pull the first and second correction anchors 18A, 18B toward the first and second tensioners 20A, 20B, and thus the stabilizing member 12 thereby exerting a derotational and/or lateral translational force on the target region 24A. By adjusting the second tensioner 20B, the effective length of the third connector 22C can also be shortened in order to apply a compressive force between the third and fourth vertebrae 26C, 26D along the third connector 22C, where the third correction anchor 18C acts as a guide to help ensure that the third connector 22C is maintained at a desired path along the spinal column 24.

In some embodiments, the compressive force is generally directed along a side of the spinal column 24 opposite the stabilizing member 12. For example, as shown in FIG. 1, the compressive force is directed along the first side 24B of the spinal column 24 (in this case, the convex aspect of the target region 24A) where the stabilizing member 12 is generally situated on the opposite side of the spinal column 24 (in this case, the concave aspect of the target region 24A). In other words, according to some embodiments, the third connector 22C extends at a lateral offset in the medial-lateral direction from the longitudinal axis Y such that the second connector is offset toward the first side 24B of the spinal column 24 which corresponds to a defective, lateral convex curvature of the spinal column 24.

Various other embodiments are treated with reference to FIGS. 7-10, which are schematic drawings of second through fifth systems 200, 300, 400, 500, respectively. As described in greater detail, the systems 200, 300, 400, 500 are shown in association with spinal columns having vertebrae exhibiting uneven growth.

Figure 7:
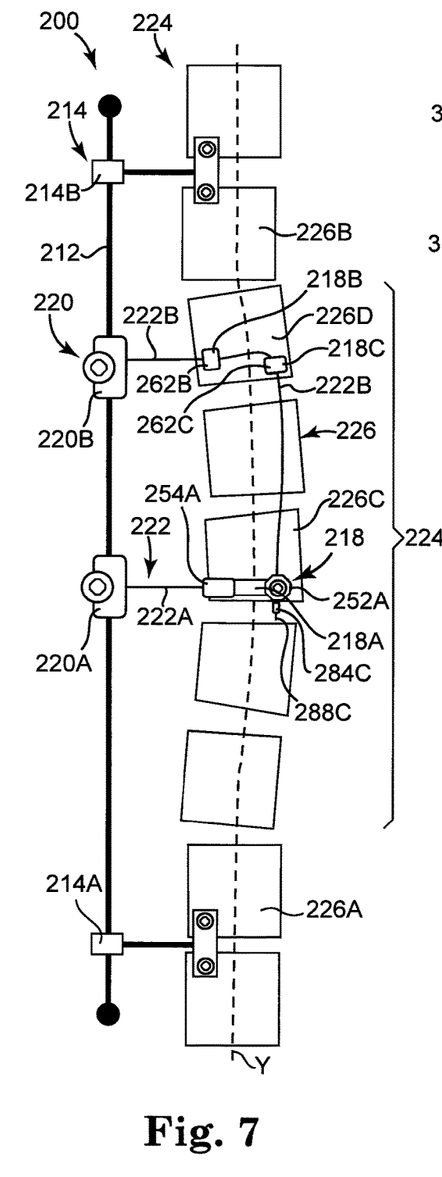
FIG. 7 is a diagrammatical view showing a second system for treating a spinal defect, according to some embodiments.

The second system 200 shown in FIG. 7 optionally includes various components similar to those previously described. In some embodiments, the system 200 includes a stabilizing member 212; a plurality of stabilizing anchors 214 including a first stabilizing anchor 214A and a second stabilizing anchor 214B; a plurality of correction anchors 218 including a first correction anchor 218A, a second correction anchor 218B, and a third correction anchor 218C; a plurality of tensioners 220 including a first tensioner 220A and a second tensioner 220B; and a plurality of connectors 222 including a first connector 222A and a second connector 222B.

As shown, the system 200 is secured to a spinal column 224 formed of a plurality of vertebrae 226, including a first vertebra 226A, a second vertebra 226B, a third vertebra 226C, and a fourth vertebra 226D, the spinal column 224 having a target region 224A tending to exhibit defective curvature.

In some embodiments, the first correction anchor 218A is substantially similar to the correction anchor 18A of the system 10 while the second and third correction anchors 218B, 218C are both substantially similar to the third correction anchor 18C of the system 10. The stabilizing member 212, stabilizing anchors 214, tensioners 220, and connectors 222 are optionally substantially similar to the stabilizing member 12, stabilizing anchors 14, tensioners 20 and connectors 22 of the system 10.

As shown in FIG. 7, in some embodiments the first and second stabilizing anchors 214A, 214B are secured to support vertebrae, such as the first and second vertebrae 226A, 226B, respectively, which reside on opposing ends of the target region 224A. The stabilizing member 212 is received by the stabilizing anchors 212 to provide stabilizing points from which to exert corrective forces on the target region 224A of the spinal column 224. The first and second tensioners 220A, 220B are mounted to the stabilizing member 212 and the first correction anchor 218 is secured to the third vertebra 226C with the first connector 222A forming a connection between the first correction anchor 218A and the first tensioner 220A in a manner similar to that previously described (e.g., through a terminal coupler 254A of the first correction anchor 218A). The second and third correction anchors 218B, 218C are secured to the fourth vertebra 226D, the second correction anchor 218B being on the convex side of the spinal column 224 and the third correction anchor 218C being opposite the second correction anchor 218B on the concave side of the spinal column 224.

The second connector 222B is secured to the second tensioner 220A, extending from the second tensioner 220A through a receptacle portion 262B of the second correction anchor 218B, a receptacle portion 262C of the second correction anchor 218C, and a head 252A of the first correction anchor 218A, the second end 284B of the second connector 222B having an end piece 288B for substantially preventing the second connector 222B from being drawn back through the head 252A of the first correction anchor 218A. As shown, the second connector 222B forms a connection between the stabilizing member 12 and the first correction anchor 218A, as well as between the correction anchors 218A, 218B, 218C, respectively, and extends along one side of the spinal column 24 between the first and third correction anchors 218A, 218C, for example being laterally offset in the medial-lateral direction from the longitudinal axis Y. In some embodiments, the second connector is offset toward the side of the spinal column 24 corresponding to a defective, lateral convex curvature of the spinal column 24.

In some embodiments, adjustment of the first tensioner 220A to shorten an effective length of the first connector 222A results in a derotational and/or translational force on the target region 224A and more specifically the third vertebra 226C. In turn, adjustment of the second tensioner 220B to shorten an effective length of the second connector 222B tensions the connection between the stabilizing member 12 and the first correction anchor 218A, resulting in a compressive force between the third and first correction anchors 218C, 218A, and thus between the third and fourth vertebrae 226C, 226D. In some embodiments, shortening of the effective length of the second connector 222B also results in a derotational and/or translational force on the defect region 224A, and more specifically the fourth vertebra 226D, as the second connector 222B is pulled against and engages the second and/or third correction anchors 218B, 218C.

The compressive force between the third and fourth vertebrae 226C, 226D is optionally used to manage or modulate growth of the spinal column 224 between those vertebrae. In particular, the vertebrae 226 in the target region 224A are shown to have grown unevenly, being taller in height at the convex side of the spinal column 224 compared to the concave side of the spinal column 224. Such uneven growth often corresponds to a defective curvature associated with scoliosis, for example. In particular, the vertebrae 226 become less dense and taller on the convex side of the defective curvature. By selectively compressing the vertebrae 226 along the convex side where the vertebrae 226 have become inappropriately thickened, it is contemplated that the vertebrae 226 in the defective region 224A will begin to exhibit more normal proportions. In particular, the side under compression should slow vertebral body growth, while helping decompress the concave side, thus helping increase growth on the concave side, allowing better proportionality in the vertebral segment(s).

Figure 8:
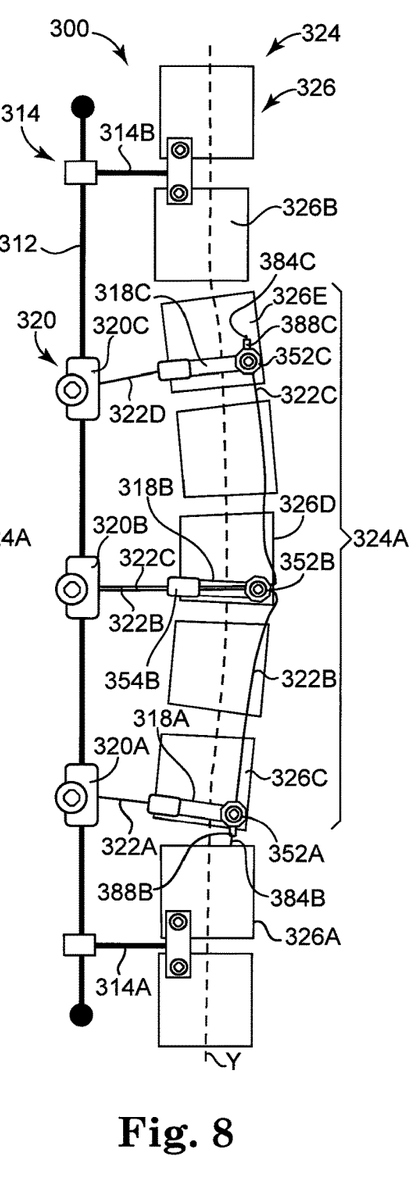
FIG. 8 is a diagrammatical view showing a third system for treating a spinal defect, according to some embodiments.

The third system 300 shown in FIG. 8 optionally includes various components similar to those previously described. In some embodiments, the system 300 includes a stabilizing member 312; a plurality of stabilizing anchors 314 including a first stabilizing anchor 314A and a second stabilizing anchor 314B; a plurality of correction anchors 318 including a first correction anchor 318A, a second correction anchor 318B, and a third correction anchor 318C; a plurality of tensioners 320 including a first tensioner 320A, a second tensioner 320B, and a third tensioner 320C; and a plurality of connectors 322 including a first connector 322A, a second connector 322B, a third connector 322C, and a fourth connector 322D.

As shown, the system 300 is secured to a spinal column 324 formed of a plurality of vertebrae 326, including a first vertebra 326A, a second vertebra 326B, a third vertebra 326C, a fourth vertebra 326D, a fifth vertebra 326E, a sixth vertebra 326F, and a seventh vertebra 326G, the spinal column 324 having a target region 324A tending to exhibit defective curvature.

In some embodiments, the first, second, and third correction anchors 318A, 318B, 318C are substantially similar to the correction anchor 18A of the system 10. The stabilizing member 312, stabilizing anchors 314, tensioners 320, and connectors 322 are optionally substantially similar to the stabilizing member 12, stabilizing anchors 14, tensioners 20 and connectors 22 of the system 10.

The stabilizing anchors 314 and stabilizing member 312 are secured to the spinal column 324 similarly to embodiments previously described. In some embodiments, the first and third tensioners 320A, 320C are mounted to the stabilizing member 312 and connected to the first and third correction anchors 318A, 318C and using the first and fourth connectors 322A, 322D. The tensioners 320A, 320C are used as desired to tension respective connections between the stabilizing member 312 and the correction anchors 318A, 318C by modifying effective lengths of the first and fourth connectors 322A, 322D to apply translational and/or derotational forces to the target region 324A as desired, and, in particular, the third and fifth vertebrae 326C, 326E.

The second tensioner 320B is also mounted to the stabilizing member intermediate the first and third tensioners 320A, 320C. The second tensioner 320B maintains the second and third connectors 322B, 322C and is adapted to modify effective lengths of the second and third connectors 322B, 322C.

In some embodiments, the second connector 322B is passed through a terminal coupler 354B of the second correction anchors 318B and through a head 352B of the second correction anchor 318B. The second connector 322B extends from the head 352B through a head 352A of the first correction member 318C. A second end 384B of the second connector 322B includes an endpiece 388B, which helps prevent the second end 384B from being pulled back through the head 352A of the first correction anchor 318A.

The third connector 322C is similarly passed through the second correction anchor 318B to the third correction anchor 318C, with a second end 384C of the third connector 322C being similarly secured relative to the third correction anchor 318C.

As previously noted, the second tensioner 320B is adapted to modify the effective lengths of the second and third connectors 322B, 322C. In some embodiments, the second and third connectors 322B, 322C are wrapped onto a common spool (not shown) of the second tensioner 320B such that they are concurrently spooled upon actuation of the second tensioner 322B. In other embodiments, the second tensioner 320B is configured for independent actuation of the second and third connectors 322B, 322C (e.g., using multiple spools) and/or different actuation rates of the second and third connectors 322B, 322C (e.g., using different diameter spools). In still other embodiments, the second and third connectors 322B, 322C are secured to a common tether (not shown) that is spooled into the second tensioner 320B.

Upon reducing the effective lengths of the second and third connectors 322B, 322C, compressive forces are directed from each of the third and fifth vertebrae 326C, 326E toward the fourth vertebra 326D along the second and third connectors 322B, 322C, respectively.

Similarly to the first and second systems 10, 200, the compressive forces between the third and fourth vertebrae 326C, 326D and the fifth and fourth vertebrae 326E, 326D are optionally used to manage or modulate growth of the spinal column 324 between those vertebrae 326, such as to modify or correct uneven growth associated with defective spinal curvature.

Figures 9, 10:
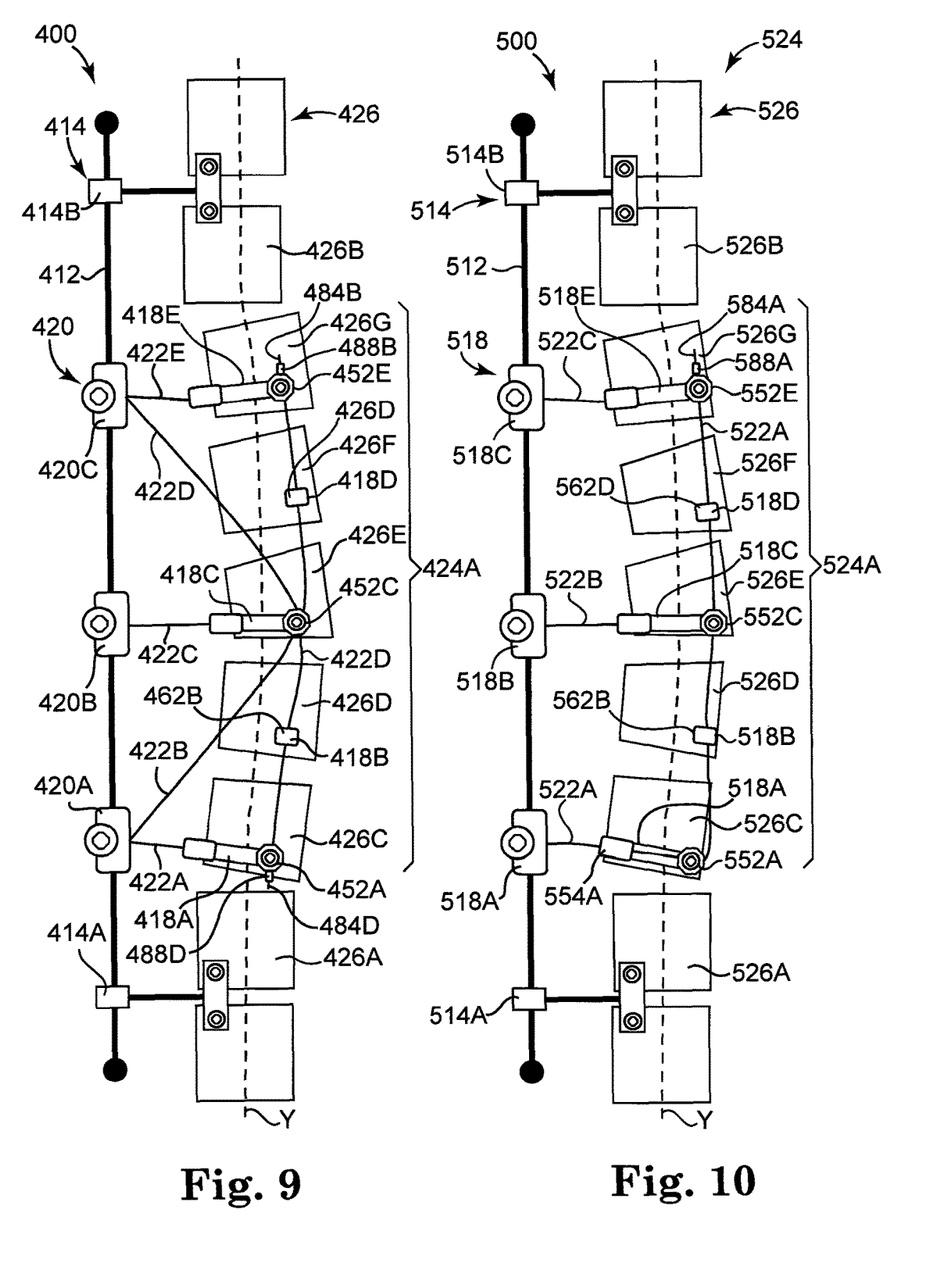
FIG. 9 is a diagrammatical view showing a fourth system for treating a spinal defect, according to some embodiments.
FIG. 10 is a diagrammatical view showing a fifth system for treating a spinal defect, according to some embodiments.

The fourth system 400 shown in FIG. 9 optionally includes various components similar to those previously described. In some embodiments, the system 400 includes a stabilizing member 412; a plurality of stabilizing anchors 414 including a first stabilizing anchor 414A and a second stabilizing anchor 414B; a plurality of correction anchors 418 including a first correction anchor 418A, a second correction anchor 418B, a third correction anchor 418C, a fourth correction anchor 418D, and a fifth correction anchor 418E; a plurality of tensioners 420 including a first tensioner 420A, a second tensioner 420B, and a third tensioner 420C; and a plurality of connectors 422 including a first connector 422A, a second connector 422B, a third connector 422C, a fourth connector 322D, and a fifth connector 422E.

As shown, the system 400 is secured to a spinal column 424 formed of a plurality of vertebrae 426, including a first vertebra 426A, a second vertebra 426B, a third vertebra 426C, a fourth vertebra 426D, a fifth vertebra 426E, a sixth vertebra 426F, and a seventh vertebra 426G, the spinal column 424 having a target region 424A tending to exhibit defective curvature.

In some embodiments, the first, third, and fifth correction anchors 418A, 418C, 418E are substantially similar to the correction anchor 18A of the system 10, while the second and fourth correction anchors 418B, 418D are substantially similar to the third correction anchor 18C of the system 10. The stabilizing member 412, stabilizing anchors 414, tensioners 420, and connectors 422 are optionally substantially similar to the stabilizing member 12, stabilizing anchors 14, tensioners 20 and connectors 22 of the system 10.

The stabilizing anchors 414 and stabilizing member 412 are secured to the spinal column 424 similarly to embodiments previously described. In some embodiments, the first, second, and third tensioners 420A, 420B, 420C are mounted to the stabilizing member 412 form connections to the first, third, and fifth correction anchors 418A, 418C, 418E using the first, third, and fifth connectors 422A, 422C, 422E. The tensioners 420A, 420B, 420C are used as desired to modify effective lengths of the first, third, and fifth connectors 422A, 422C, 422E to apply translational and/or derotational forces to the target region 424A, and in particular the third, fifth, and seventh vertebrae 426C, 426E, 426G via the first, third, and fifth correction anchors 418A, 418C, 418E.

The first and third tensioners 420A, 420C also maintain the second and fourth connectors 422B, 422D and are adapted to modify effective lengths of the second and fourth connectors 422B, 422D, respectively. As referenced in association with other embodiments, the first and third tensioners 420A, 420C are adapted for independent or concurrent spooling of multiple connectors 422 as desired.

In some embodiments, the second connector 422B is passed through a head 452C of the third correction anchor 418C, through a receptacle portion 462D of the fourth correction anchor 418D, and through a head 452E of the fifth correction anchor 418E.

The fourth connector 422D is similarly passed through or around the head 452C of the third correction anchor 418C, through a receptacle portion 462B of the second correction anchor 418B, and through a head 452A of the first correction anchor 418A. Second ends 484B, 484D of each of the second and fourth connectors 422B, 422D include endpieces 488B, 488D, which help prevent the second ends 484B, 484D from being pulled back through the heads 452A, 452E of the first and fifth correction anchors 418A, 418E, respectively.

Upon actuation of the first and third tensioners 420A, 420C to shorten the effective lengths of the second and fourth connectors 422B, 422D, compressive forces are directed from each of the third and seventh vertebrae 426C, 426G toward the fifth vertebra 426E along the second and fourth connectors 422B, 422D, respectively.

Similarly to the first, second, and third systems 10, 200, 300, the compressive forces are optionally used to manage or modulate growth of the spinal column 424 between those vertebrae 426, such as to modify or correct uneven growth associated with defective spinal curvature.

The fifth system 500 shown in FIG. 10 optionally includes various components similar to those previously described. In some embodiments, the system 500 includes a stabilizing member 512; a plurality of stabilizing anchors 514 including a first stabilizing anchor 514A and a second stabilizing anchor 514B; a plurality of correction anchors 518 including a first correction anchor 518A, a second correction anchor 518B, a third correction anchor 518C, a fourth correction anchor 518D, and a fifth correction anchor 518E; a plurality of tensioners 520 including a first tensioner 520A, a second tensioner 520B, and a third tensioner 520C; and a plurality of connectors 522 including a first connector 522A, a second connector 522B, and a third connector 522C.

As shown, the system 500 is secured to a spinal column 524 formed of a plurality of vertebrae 526, including a first vertebra 526A, a second vertebra 526B, a third vertebra 526C, a fourth vertebra 526D, a fifth vertebra 526E, a sixth vertebra 526F, and a seventh vertebra 526G, the spinal column 524 having a target region 524A tending to exhibit defective curvature.

In some embodiments, the first, third, and fifth correction anchors 518A, 518C, 518E are substantially similar to the correction anchor 18A of the system 10, while the second and fourth correction anchors 518B, 518D are substantially similar to the third correction anchor 18C of the system 10. The stabilizing member 512, stabilizing anchors 514, tensioners 520, and connectors 522 are optionally substantially similar to the stabilizing member 12, stabilizing anchors 14, tensioners 20 and connectors 22 of the system 10.

The stabilizing anchors 514 and stabilizing member 512 are secured to the spinal column 524 similarly to embodiments previously described. In some embodiments, the first, second, and third tensioners 520A, 520B, 520C are mounted to the stabilizing member 512 and form connections with the first, third, and fifth correction anchors 518A, 518C, 518E using the first, second, and third connectors 522A, 522B, 522C. The tensioners 520A, 520B, 520C are used as desired to modify effective lengths of the first, second, and third connectors 522A, 522C, 522E to apply translational and/or derotational forces to the target region 524A, and in particular the third, fifth, and seventh vertebrae 526C, 526E, 526G via the first, third, and fifth correction anchors 518A, 518C, 518E.

The first tensioner 520A and first connector 522A also apply a compressive force to the spinal column 524. In particular, the first connector 522A extends through a terminal coupler 554A to the head 552A of the first correction anchor 518A and is then directed superiorly by the head 552A through a receptacle 562B of the second correction anchor 518B, a head 552C of the third correction anchor 518C, a receptacle 562E of the fourth correction anchor 518E, and through a head 552E of the fifth correction anchor 518E. A second end 584A of the first connector 522A includes an endpiece 588A to help prevent the second end 584A from pulling back through the fifth correction anchor 518E. Upon tensioning the first connector 522A, the target region 524A is compressed along the first connector 522A. In particular, the third through seventh vertebrae 526C-526G are placed in compression. Moreover, the first connector 522A tightens against the head 552A of the first correction anchor 518A, such that a translational and/or derotational force is applied at the terminal coupler 554A of the first correction anchor 518A.

Similarly to the first, second, third, and fourth systems 10, 200, 300, 400 the compressive force is optionally used to manage or modulate growth of the spinal column 524 between those vertebrae 526, such as to modify or correct uneven growth associated with defective spinal curvature.

The various systems and methods provided according to the foregoing detailed description include features that are interchangeable as appropriate. In view of the foregoing, systems, methods, and devices according to some embodiments provide for exerting a gross corrective force (translational and/or rotational) on a spinal column in combination with exerting a compressive force selectively applied along a side of the spinal column, for example a side generally opposite a direction of correction. Some embodiments relate to translating application of a corrective force on a spinal column (translation and/or derotation) to an axial force to selectively limit vertebral growth. Various other features and advantages are contemplated.

For example, various modifications and additions can be made to the exemplary embodiments discussed without departing from the scope of the present invention. While the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What is claimed is:

1. A spinal management system comprising:
    a stabilizing member adapted to extend substantially longitudinally along a target region of a spine tending to exhibit a defective curvature;
    a set of stabilizing anchors adapted for fixation to vertebrae and to receive the stabilizing member to secure the stabilizing member against substantial transverse translation relative to the vertebrae;
    a first correction anchor adapted for fixation to a vertebra;
    a second correction anchor adapted for fixation to a vertebra;
    at least one tensioner coupled to the stabilizing member; and
    a connector having a first portion extending between the at least one tensioner and the first correction anchor and a second portion extending substantially longitudinally directly between the first and second correction anchors, the second portion configured to draw the second correction anchor towards the first correction anchor when the connector is tensioned such that a compressive force is exerted along the second portion, directly between the first and second correction anchors.

2. The system of claim 1, wherein the connection is a continuous flexible cable.

3. The system of claim 1, wherein the tensioner is movable about the stabilizing member.

4. A spinal management system comprising:
    a stabilizing member adapted to extend substantially longitudinally along a target region of a spine tending to exhibit a defective curvature;
    a set of stabilizing anchors adapted for fixation to vertebrae and to receive the stabilizing member to secure the stabilizing member against substantial transverse translation relative to the vertebrae;
    a first correction anchor adapted for fixation to a vertebra;
    a second correction anchor adapted for fixation to a vertebra;
    at least one tensioner coupled to the stabilizing member, the at least one tensioner including a housing; and
    a connector having a first portion extending between the at least one tensioner and the first correction anchor and a second portion extending substantially longitudinally directly between the first and second correction anchors and adapted such that when the connector is tensioned a compressive force is exerted along the second portion, directly between the first and second correction anchors.

5. The system of claim 4, wherein the housing includes a lumen configured to receive the stabilizing member.

6. The system of claim 4, wherein the housing includes a reel, wherein the connector is attached to the reel.

7. The system of claim 6, wherein the housing includes a circumferential gear surrounding the reel.

8. The system of claim 7, wherein the housing includes a vertical gear in contact with the circumferential gear.

9. A spinal management system comprising:
    a stabilizing member adapted to extend along a target region of a spine;
    a set of stabilizing anchors adapted for fixation to vertebrae and to receive the stabilizing member to secure the stabilizing member against substantial transverse translation relative to a longitudinal axis of the spine;
    a first correction anchor adapted for fixation to a first vertebra;
    a second correction anchor adapted for fixation to a second vertebra;
    at least one tensioner coupled to the stabilizing member; and
    a connector having a first portion extending between the at least one tensioner and the first correction anchor and a second portion extending substantially longitudinally directly between the first and second correction anchors, the second portion configured to draw the second correction anchor towards the first correction anchor when the connector is tensioned such that a compressive force is exerted along the second portion, directly between the first and second correction anchors.

* * * * *